US011056237B2

(12) United States Patent
Fidone et al.

(10) Patent No.: US 11,056,237 B2
(45) Date of Patent: *Jul. 6, 2021

(54) SYSTEM AND METHOD FOR DETERMINING AND INDICATING VALUE OF HEALTHCARE

(71) Applicant: Healthcare Value Analytics, LLC, Lufkin, TX (US)

(72) Inventors: George Fidone, Lufkin, TX (US); G. Edward Powell, Jr., Nashville, TN (US); Norman E. White, Austin, TX (US); Van Marshall, Sunnyvale, TX (US); Mark Lane, Franklin, TN (US); Brett M. Rader, Round Rock, TX (US); Justin Craig Fidone, West Linn, OR (US); Michael Williams, The Hills, TX (US)

(73) Assignee: Health Value Analytics, Inc., Brentwood, TN (US)

(*) Notice: Subject to any disclaimer, the term of this patent is extended or adjusted under 35 U.S.C. 154(b) by 680 days.

This patent is subject to a terminal disclaimer.

(21) Appl. No.: 15/892,256

(22) Filed: Feb. 8, 2018

(65) Prior Publication Data

US 2018/0166172 A1 Jun. 14, 2018

Related U.S. Application Data

(63) Continuation-in-part of application No. 15/590,382, filed on May 9, 2017, which is a continuation-in-part
(Continued)

(51) Int. Cl.
*G16H 40/20* (2018.01)
*G16H 50/20* (2018.01)
(Continued)

(52) U.S. Cl.
CPC .......... *G16H 50/20* (2018.01); *G16H 10/60* (2018.01); *G16H 40/20* (2018.01); *G16H 50/30* (2018.01); *G16H 15/00* (2018.01); *Y02A 90/10* (2018.01)

(58) Field of Classification Search
CPC .............................. G16H 10/60; G16H 50/20
(Continued)

(56) References Cited

U.S. PATENT DOCUMENTS

2006/0173706 A1* 8/2006 Allin ................ G06Q 40/025
705/38
2006/0223504 A1* 10/2006 Ishak ................ H04W 52/0251
455/414.1
(Continued)

OTHER PUBLICATIONS

Alex A. T. Bui, Denise R. Aberle, and Hooshang Kangarloo, TimeLine: Visualizing Integrated Patient Records, IEEE Transactions on Information Technology in Biomedicine, vol. 11, No. 4, Jul. 2007 (Year: 2007).*

*Primary Examiner* — Joshua B Blanchette

(57) ABSTRACT

A processor-implemented method for determining and indicating values of medical treatment plans, includes the processor creating value baselines comprising health metric values for approved plans of care; detecting an activity indicating a patient-related event during a visit associated with a patient; generating a health value continuum based on the visit; generating a comparison of the health value continuum to a value baseline; and providing data and instructions to display on a display page, a representation of the health value continuum to value baseline comparison.

23 Claims, 28 Drawing Sheets

Related U.S. Application Data of application No. 15/350,910, filed on Nov. 14, 2016, which is a continuation-in-part of application No. 15/177,058, filed on Jun. 8, 2016.

(51) Int. Cl.
*G16H 10/60* (2018.01)
*G16H 50/30* (2018.01)
*G16H 15/00* (2018.01)

(58) Field of Classification Search
USPC .......................................... 705/2, 3
See application file for complete search history.

(56) References Cited

U.S. PATENT DOCUMENTS

| | | | | |
|---|---|---|---|---|
| 2008/0172251 | A1* | 7/2008 | Reichert | G16H 40/20 705/2 |
| 2009/0156303 | A1* | 6/2009 | Kiely | G07F 17/3239 463/29 |
| 2013/0275793 | A1* | 10/2013 | Yagi | G06F 1/3209 713/323 |
| 2013/0304499 | A1* | 11/2013 | Rangadass | G06Q 10/063114 705/2 |

* cited by examiner

SYSTEM AND METHOD FOR DETERMINING AND INDICATING VALUE OF HEALTHCARE

CROSS-REFERENCE TO RELATED APPLICATIONS

This application is a continuation-in-part of U.S. patent application Ser. No. 15/590,382, SYSTEM AND METHOD FOR DETERMINING AND INDICATING VALUE OF HEALTH CARE," filed May 9, 2017, which is a continuation-in-part of U.S. patent application Ser. No. 15/350,910, entitled "SYSTEM AND METHOD FOR DETERMINING AND INDICATING VALUE OF HEALTH CARE," filed Nov. 14, 2016, which is a continuation-in-part of U.S. patent application Ser. No. 15/177,058 entitled "SYSTEM AND METHOD FOR DETERMINING AND INDICATING VALUE OF HEALTH CARE," filed Jun. 8, 2016. The contents of the above-identified patent documents are incorporated herein by reference.

BACKGROUND

As the cost of providing health care continues to increase at an unsustainable rate, health care providers (especially physicians) are increasingly being held responsible for controlling cost in an effort to provide high quality care while controlling costs. Drivers of this shift in responsibility include the federal government (Medicare, Medicaid, VA, CHiPs), state governments, third party payers (both for-profit and not-for-profit), and Accountable Care Organizations (ACOs) as well as individual hospitals and medical groups. Increasingly, health care providers are being asked to share in the financial risk in providing medical care.

SUMMARY

A processor-implemented method for determining and indicating values of medical treatment plans, includes the processor creating value baselines comprising health metric values for approved plans of care; detecting an activity indicating a patient-related event during a visit associated with a patient; generating a health value continuum based on the visit; generating a comparison of the health value continuum to a value baseline; and providing data and instructions to display on a display page, a representation of the health value continuum to value baseline comparison.

A method for determining and indicating values of medical treatment plans, the method executed over a client-server architecture in a local private network, includes a server creating value baselines comprising health metric values for approved plans of care; the server receiving a detected activity related to medical care for a patient having an associated diagnosis during a visit of the patient; and the server: determining the activity warrants generating a health value continuum, generating a health value continuum corresponding to the diagnosis, generating a comparison of the health value continuum to the value baseline, and providing data and instructions to the client to display a representation of the health value continuum to value baseline comparison.

A method executed by a processor of a health value analytics system in communication with a device external to the health value analytics system, comprising the processor monitoring for and receiving an indication of a patient-related event from the external device, the patient-related event referencing a visit of a patient; and based on a visit reference, the processor: determining a need to and generating a health value continuum: generating of a comparison of the health value continuum to a value baseline for an approved plan of care for the patient, and providing of data and instructions to display on a display page at the external device, a representation of the health value continuum to value baseline comparison.

DESCRIPTION OF THE DRAWINGS

The detailed description refers to the following drawings, in which like numerals refer to like objects, and in which:

FIGS. 8A-8C illustrate example displays for determining and indicating value of health care that may be generated by the systems of FIGS. 5A-5F;

DETAILED DESCRIPTION

Figure 1:
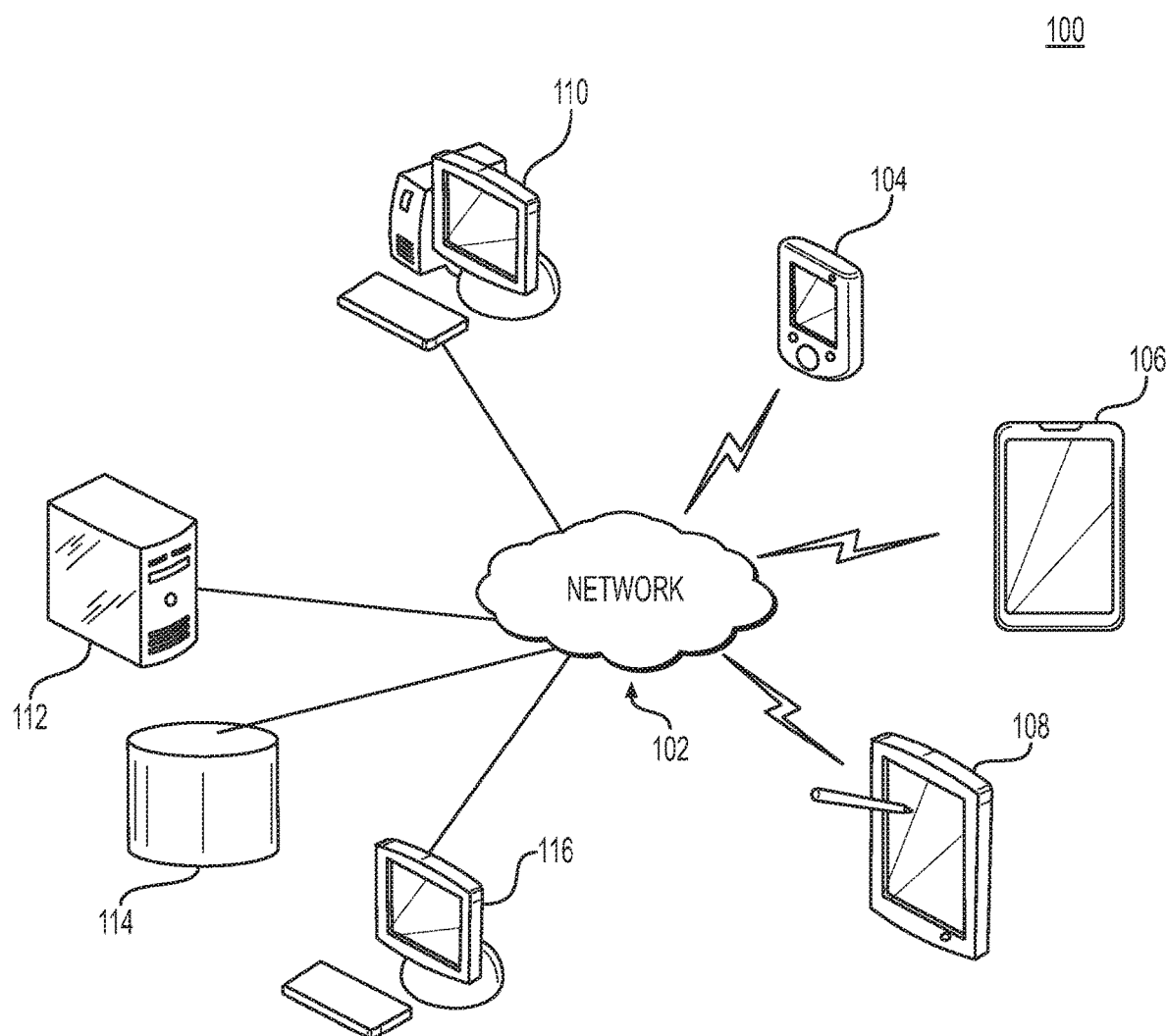
FIG. 1 illustrates an example system for determining and indicating value of health care, according to this disclosure.

Large medical facilities (e.g., hospitals) may employ large, secure, and carefully regulated and monitored electronic medical record systems (EMR) (sometimes known as electronic health records (EHR) systems), and the EMR systems may use a dedicated EMR server to access a large EMR database that contains the electronic medical records. End users (for example, physicians, nurses, other health care providers, and other hospital staff) may interact with the EMR database using, for example, laptop and desktop computers, work stations, notepads, and smartphones. In some situations, end users require rapid, real-time access to the EMR database. At all times, end users require accurate and up-to-date information from the EMR system. The resulting high demand for information, conveyed in the form of requests from end user devices, and suppled in the form of responses from the EMR system, may overload the EMR system and result in slower than desired information retrieval.

For example, health care providers may lack information regarding the costs of services provided within a hospital or medical center. While health care providers (e.g., physicians) often are cognizant of their office charges and perhaps even their daily visit charges in a hospital setting, they typically do not know the hospital's costs associated with providing service to their patients. In addition, the providers usually do not know the baseline range of historical costs to treat a particular condition or the expected overall reimbursement that a health care facility may receive for patients being treated at the facility.

On the other hand, hospitals and other health care facilities may use nationally accepted formulas for each hospitalization of a patient to arrive at an expected payment/reimbursement. Additionally, hospitals generally maintain a comprehensive charge list of the costs of materials and time for each component of care delivered. Physicians and other health care providers typically lack access to these two hospital-based components of accounting, yet these components are major drivers of the cost and value of health care delivered.

Currently, there is no mechanism for combining the available accounting information from discrete information sources for all types of care, processing this information, and then presenting the information to a health care provider in real-time, on-demand, in a way that helps the health care provider determine an appropriate plan of care. Current methods of reporting are incomplete, inaccurate, delayed (i.e., not real-time), and/or cumbersome (e.g., information not presented in a useful, easily readable manner).

The determination of "value" has become the new mandate from businesses, payers, and the patients themselves, each of whom look to reduce health care costs. The market is ready for a system that can determine and monitor the value of health care being delivered in multiple settings from the point of diagnosis through the last service provided, whether inpatient or outpatient.

To address these issues, embodiments of this disclosure provide systems and methods for determining and indicating value of health care. The disclosed systems and methods provide and process health care cost and value information on a regular, ongoing basis, and/or on an episodic or ad hoc basis, and may automatically update the information when changes are needed or desired. A health care provider may see where the value of the patient's health care falls within a value continuum after or as a result of every input.

The disclosed systems help health care providers monitor, manage, and maximize value in the delivery of care. In some embodiments, the disclosed systems are capable of determining the baseline range of costs to treat a patient diagnosis. The systems receive information relating to a plurality of health care services associated with a patient. The systems have the ability to associate a cost with each of the health care services and the ability to aggregate the costs for the health care services. In addition, the disclosed systems are capable of presenting the service cost and value data to the health care provider in a way that the value data may be used to determine an appropriate plan of care for the patient.

FIG. 1 illustrates an example system 100 for determining and indicating value of health care. As shown in FIG. 1, the system 100 includes a network 102. The network 102 provides a structure to facilitate communication between different devices or systems. The network 102 may provide any suitable communication links, such as wired, wireless, fiber optic links, or the like. In an embodiment, the network 102 includes a combination of networks, such as the Internet, one or more cellular communication networks, and one or more local or wide area networks (which may support wired or wireless communications). A local or wide area network may be a private network or virtual private network.

Multiple end user devices 104-110 communicate via the network 102. The user devices 104-110 generally denote devices used by health care providers or their assistants to access, provide, update, or remove information associated with patient electronic medical records (EMRs), health care costs, and health care value measurements. The user devices 104-110 include fixed or mobile devices that may communicate over wired, wireless, or other connections with at least one of the networks 102. In this example, the user devices 104-110 include a personal digital assistant 104, a smartphone 106, a tablet computer 108, and a desktop or laptop computer 110. Any other or additional user devices may be used in the system 100, and the system 100 may support interaction with any number of user devices.

One or more servers 112 also may communicate over the network 102. Each server 112 may represent a computing device that processes information associated with patient EMRs, health care costs, and value measurements, as described in greater detail below. Information associated with the operations of the server 112 is stored in one or more related databases 114. For example, each server 112 retrieves and provides information about one or more patient health care records, one or more medical or health care procedures associated with the patient, and cost or reimbursement information associated with the medical or health care procedures. Different information or additional information also may be provided by each server 112. Each server 112 includes any suitable structure for providing information and interacting with user devices. The database 114 includes any suitable structure for storing information and for facilitating retrieval of information (e.g., a relational database accessible through Structured Query Language (SQL) commands).

One or more operator stations 116 may interact with the server 112. For example, an operator station 116 allows health care personnel to access, provide, update, or remove information associated with patient EMRs, health care costs, and health care value measurements. Each operator station 116 includes any suitable structure supporting interaction with a server, such as a desktop computer, laptop computer, thin client, or mobile device.

As described herein, each user device 104-110 may execute an application or may access an application executed by the server 112. The application allows a user to interact with, receive information from, and provide information to, the server 112. For example, the server 112 may receive requests from the user devices 104-110 and in response to receiving requests from the user devices 104-110 provides information from the database 114. Other operations supported by the application are described herein.

Although FIG. 1 illustrates one example of a system 100 for determining and indicating value of health care, various changes may be made to FIG. 1. For example, various components in FIG. 1 may be combined, further subdivided, rearranged, or omitted and additional components may be added according to particular needs.

Figure 2:
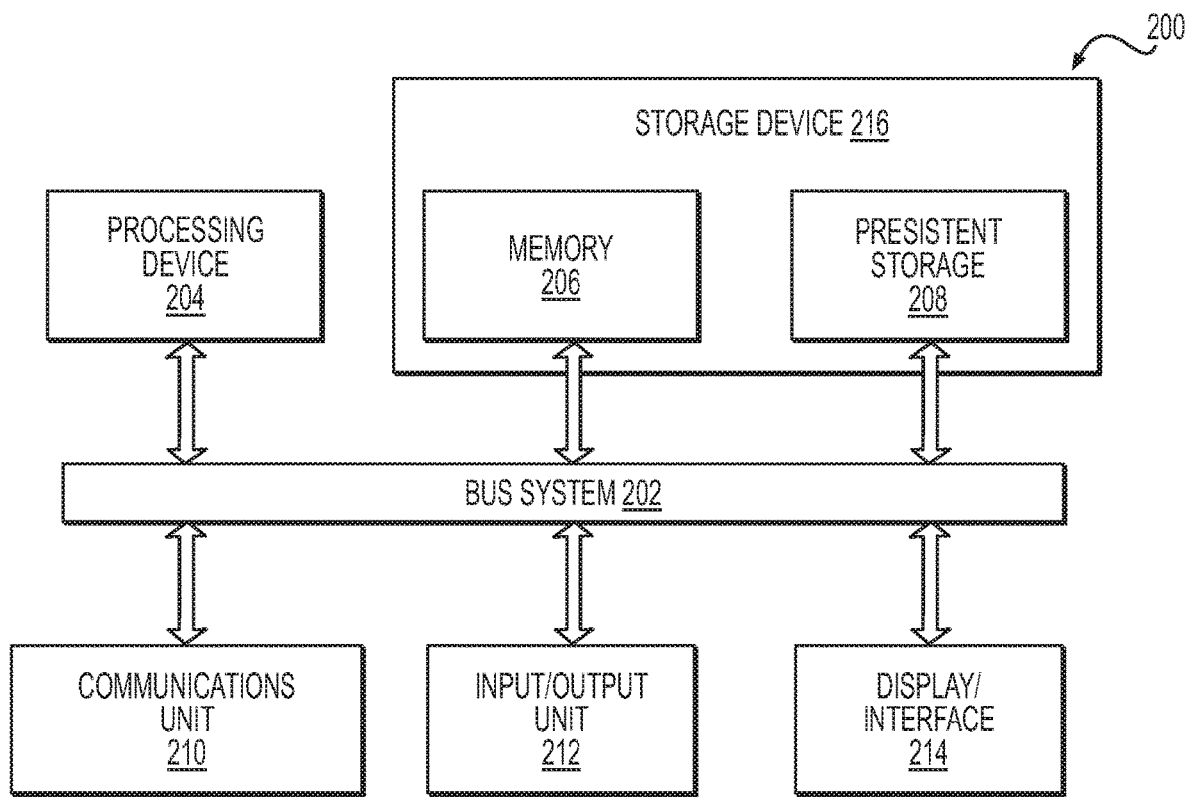
FIG. 2 illustrates an example device for use in the system of FIG. 1.

FIG. 2 illustrates an example device 200 for use in the system 100 according to this disclosure. The device 200 may represent any of the components 104-112 and 116 in FIG. 1. In this example, the device 200 includes a bus system 202. The bus system 202 supports communication between a processing device 204, a memory 206, a persistent, non-transitory computer-readable storage 208, a communications unit 210, an input/output (I/O) unit 212, and a display or display interface 214.

The processing device 204 processes software/firmware instructions, such as instructions loaded from the storage 208 into the memory 206. The processing device 204 may include a single processor, multiple processors, one or more multi-processor cores, or other type(s) of processor(s) depending on the particular implementation. As an example, the processing device 204 is implemented using a number of heterogeneous processor systems in which a main processor is present with secondary processors on a single chip. As another example, the processing device 204 is a symmetric multi-processor system containing multiple processors of a same or similar type. Any suitable processing device(s) may be used.

The memory 206 and the storage 208 are examples of storage devices that may be used in the device 200. Such storage devices may be any piece of hardware capable of storing information, such as data, program code, or other suitable information on a temporary or permanent basis. The memory 206 may be a random access memory or other volatile or non-volatile storage device(s). The storage 208 contains one or more components or devices, such as a hard drive, flash memory, optical disc, or other non-transitory computer-readable storage device(s). A storage device may be fixed or removable, such as when a removable hard drive or USB thumb drive is used.

The communications unit 210 provides for communications with other systems or devices. For example, the communications unit 210 includes a network interface card or a wireless transceiver. The communications unit 210 provides communications through physical or wireless communications links.

The I/O unit 212 allows for input and output of data using other components connected to or integrated within the device 200. For example, the I/O unit 212 provides a connection for user input through a keyboard, a mouse, a microphone, or another input device. The I/O unit 212 also sends output to a display, printer, speaker, or other output device. The I/O unit 212 alternatively includes a keyboard, a mouse, a speaker, a microphone, or another input or output device(s). If the device 200 includes a display 214, the display or display interface 214 provides a mechanism to visually present information to a user. In some user devices, the display is represented as a touchscreen.

Program code for an operating system, applications, or other programs is located in the storage device 216, which is in communication with the processing device 204 through the bus system 202. Instructions forming the programs are loaded into the memory 206 for processing by the processing device 204.

Returning to FIG. 1, as described herein, the system 100 may provide health care cost and value information on a regular, ongoing basis, or on an episodic or ad hoc basis, and may automatically update the information when changes occur. Every time a health care provider treats a patient, or otherwise orders care for a patient, the health care provider may see how the costs of his decisions relate to the overall cost objectives for a patient with a particular diagnosis. The real-time information along with robust reporting features in the system 100 advantageously provide tools to train health care providers to be more cost-conscious in making decisions about care and to provider better value in health care.

The information may be used individually (e.g., for real-time individual decision making by a health care provider) and for comparisons between health care providers and health care provider groups (e.g., using historical reporting features). For example, for an expensive procedure (e.g., a hip replacement), one health care provider group might include members who charge lower rates, but who use more expensive devices. This health care provider group may be compared against another provider group whose members charge higher rates, but who use less expensive devices. The information may be used to compare individual components of care (e.g., surgeon costs, device costs, and the like) and overall cost (e.g., the total cost for the hip replacement).

Additional details of the system 100 may be more readily understood by way of an example. For this example, consider a child who is admitted to a hospital for pneumonia. Before admission to the hospital, a health care provider (e.g., a physician) will have performed an examination and a work up of the patient (e.g., in the doctor's office, at an emergency care facility, or at another suitable location). Based on the examination, the physician has determined that hospitalization is needed for the patient. The physician writes admission orders to admit the patient to the hospital with a diagnosis of pneumonia. In addition to the pneumonia diagnosis, there may be co-morbidities. For example, the patient may have a supplemental oxygen requirement. Due to vomiting, the patient may be dehydrated and have low potassium. Thus, the primary diagnosis for the patient is acute pneumonia; secondary diagnoses are hypoxemia, dehydration, and hypokalemia.

Once a patient is admitted to a hospital or other health care facility, a clinical documentation improvement (CDI) specialist reviews the admitting physician's diagnosis, and the patient's medical history and current physical, enters the diagnoses in International Classification of Diseases (ICD) codes such as in ICD code groups ICD-9 or ICD-10, and executes a Diagnosis Related Group (DRG) grouper application to aggregate the selected ICD-9 or ICD-10 codes to produce an initial DRG code, known as a working DRG.

Estimated reimbursement information may be obtained from the working DRG. For example, a working DRG (the diagnoses determined from the medical record) may be multiplied by the relative weight of the DRG (a multiplier determined by the Centers for Medicare & Medicaid Services (CMS) that scores the severity of the DRG) and also multiplied by a "blended rate" (a CMS-determined multiplier that accounts for local cost influences including wage index of employees, percentage of indigent care provided, target populations, local salary and cost report information) to arrive at the expected reimbursement for that visit. The hospital also may maintain a "charge description master," which is a list of all the hospital's charges and costs.

In addition to (or in lieu of) expected reimbursement information, the diagnosis (e.g., from ICD-9 or ICD-10 codes), the working DRG, or other suitable diagnosis information may also be used to obtain expected cost information. For example, a range or distribution of "costs to treat" may be obtained based on a working DRG. The distribution may include a median cost to treat and a mean cost to treat. A baseline "cost to treat" distribution (and corresponding baseline median and baseline mean "cost to treat") may be determined in advance for each DRG. For some baseline distributions, the baseline median and baseline mean cost to treat are equal). These baseline "cost to treat" values may be determined empirically by examining historical costs of treatment over time at a particular facility or group of facilities, for a particular physician group, and the like. For example, baseline distribution of costs to treat for an appendectomy may be determined by examining a total cost of treatment for all appendectomies at a hospital over a two-year period. In some embodiments, the baseline cost to treat distribution may be determined directly from the ICD9 or ICD10 codes or other diagnosis information. In some embodiments, the baseline cost to treat distribution may be determined using a neural network that includes multiple inputs, such as age, gender, ICD code(s), DRG(s), time of day, and the like.

In some embodiments, the baseline cost to treat distribution may be determined based on a designed plan of care. For a particular physician group, and for a particular diagnosis, the designed plan of care may represent an authorized or approved plan of care. The designed plan of care may include components such as orders, procedures, and medications, for example. The designed plan of care then may constitute, or may be used to establish, a baseline cost to treat distribution against which the aggregated costs for a specific visit are compared, as described herein. The designed plan of care may be determined by a group of experts using evidence-based medicine or clinical best practices. For example, the designed plan of care may be determined by a governmental or regulatory agency, by a corporate in-house physician group, or by any other suitable organization or group. Such designed plans of care already have been developed, reviewed, and approved for strokes, pneumonia, heart attacks, chest pain, and other common medical issues, as known in the art. The designed plan of care may include an order set that also includes target times to perform each order.

In some cases, the baseline cost to treat for a diagnosis may be close to an expected reimbursement for the diagnosis. In other cases, the baseline cost to treat may vary substantially from the expected reimbursement. Where both baseline cost to treat and expected reimbursement are available, both information points may be valuable to the health care provider. All this information may be input into the system 100 (e.g., via one or more of the devices 104-110, 116) and may be associated with the patient's electronic medical record(s) (which may be stored in the database 114), as described herein.

Once a patient is admitted, various costs are aggregated based on the care ordered for or provided to the patient. For example, intravenous (IV) fluids may be ordered for the patient. There is a cost to the hospital for the fluids. There is an additional cost to the hospital for nursing care associated with setting up and administering the IV fluids. As another example, an antibiotic may be ordered for the patient. There is a cost to the hospital for the antibiotic. In addition, the hospital room in which the patient visit is associated with a cost. Each of these costs is included in a running schedule or running total of costs associated with the patient's hospital visit. In conventional systems, while these costs may be predetermined, the costs may not be readily available to a health care provider. In contrast, in the system 100, the orders for the IV fluids and antibiotic may be entered, and the effect of those costs for those items against the overall expected reimbursement or baseline cost to treat may be seen and evaluated before they are even administered.

Figure 3:
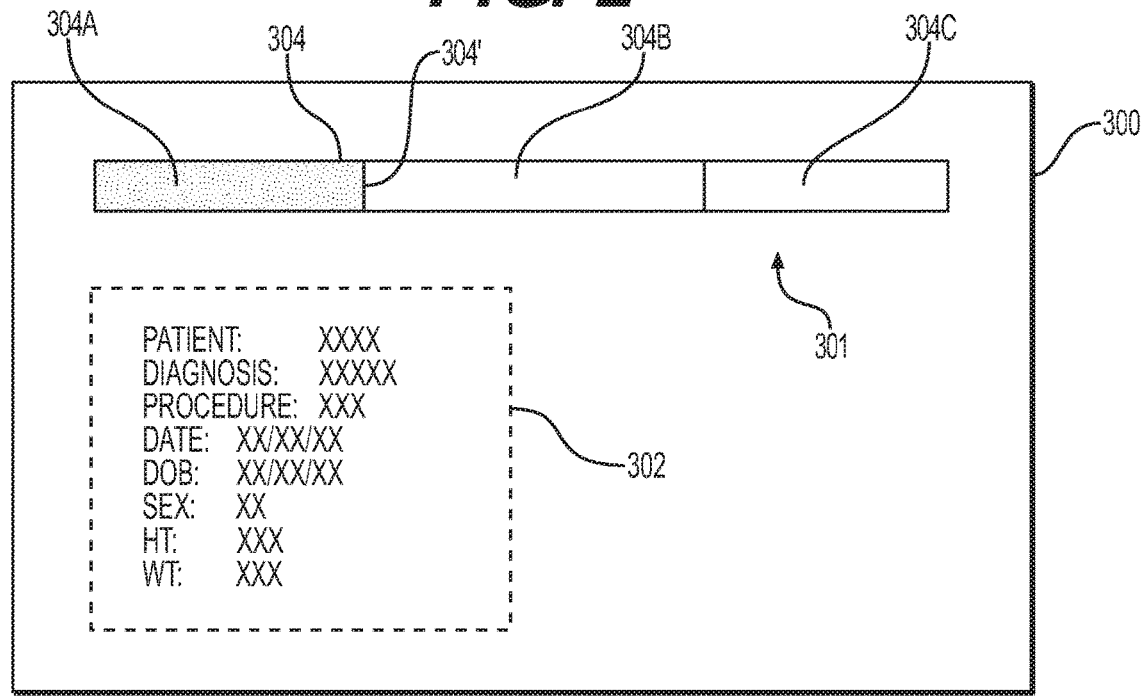
FIG. 3 illustrates an example display for determining and indicating value of health care that may be used in the system of FIG. 1.
Figure 4A:
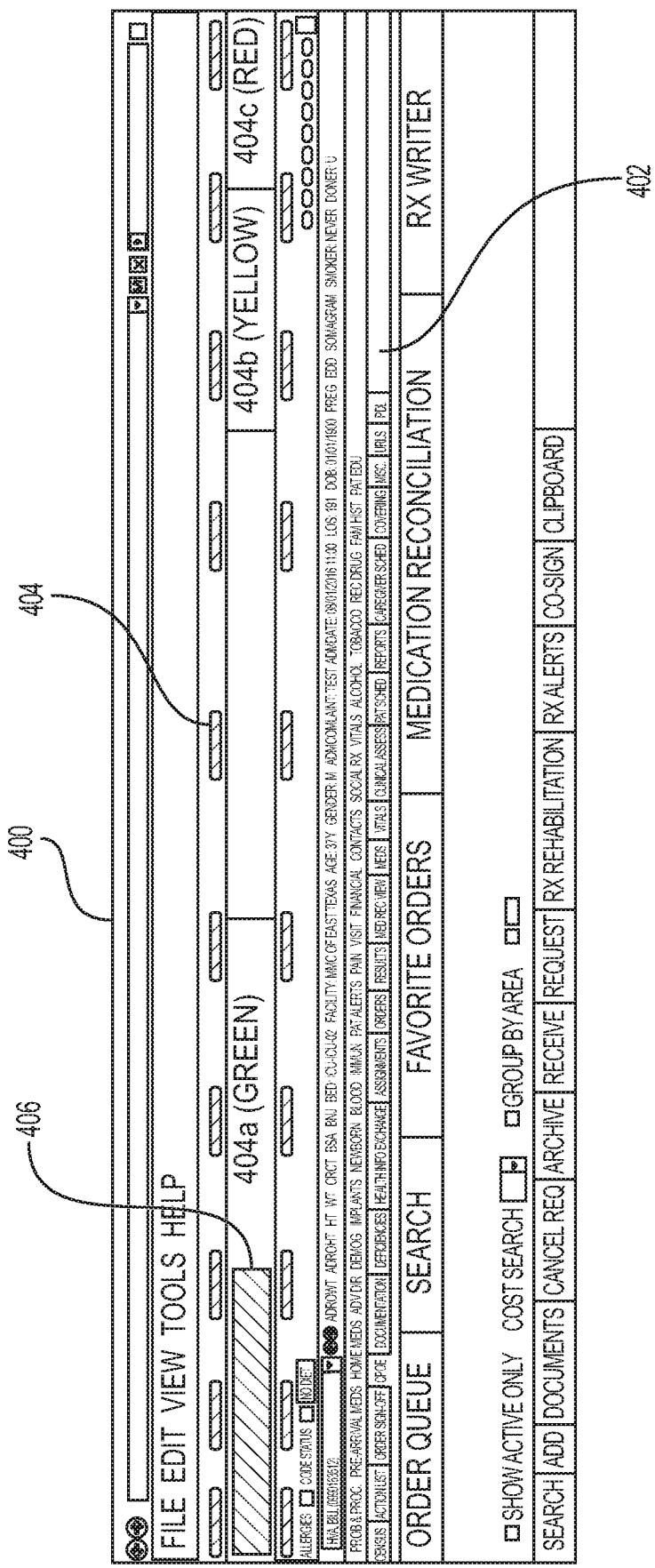
FIGS. 4A and 4B illustrate additional example displays for determining and indicating value of health care that may be used in the system of FIG. 1.
Figure 4B:
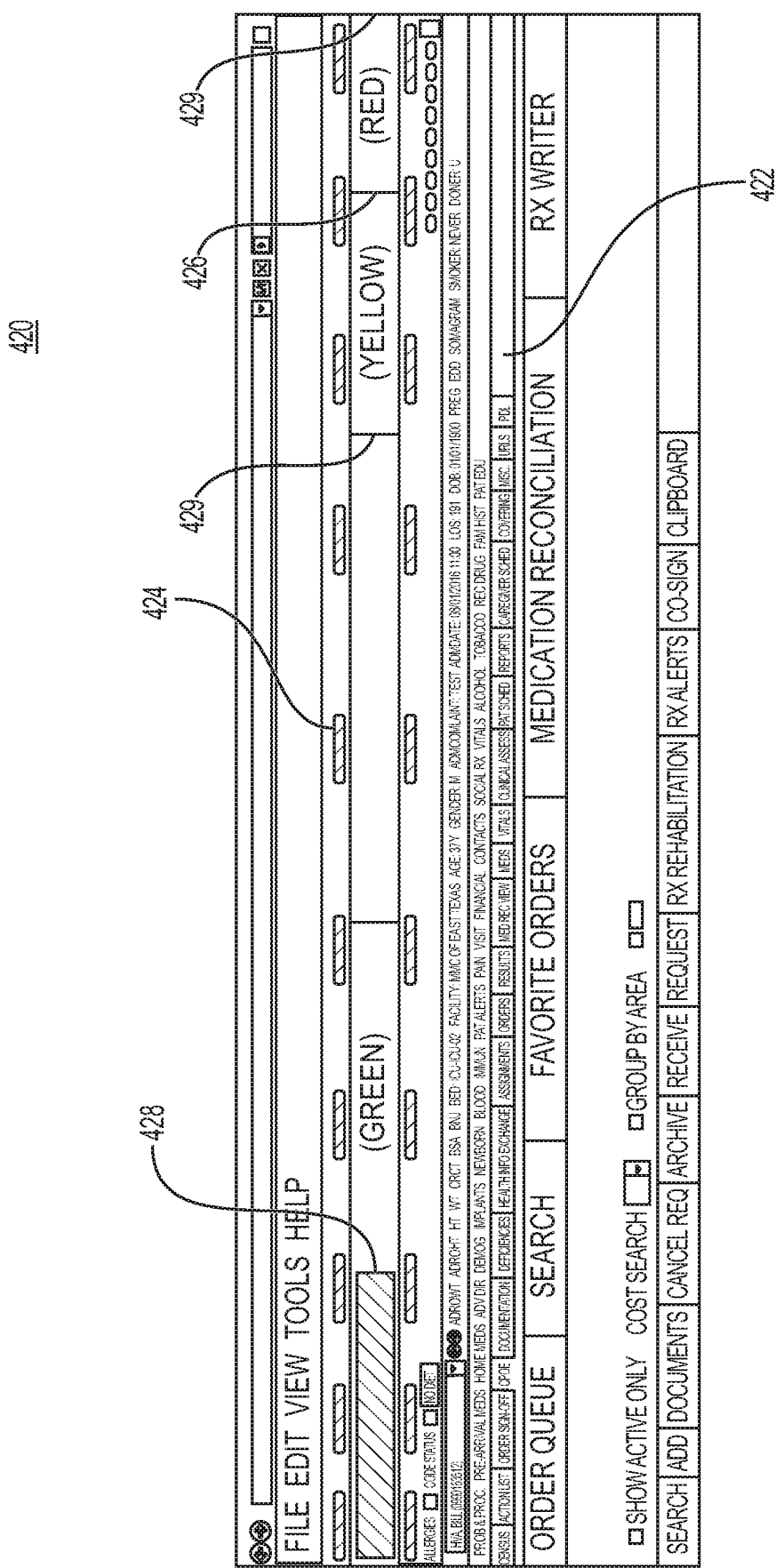

FIGS. 3, 4A and 4B provide examples of information displays that may be useful to a health care provider. One such information displays may be referred to as a health value continuum. The health value continuum may include a value bar and/or a progress bar. For example, a running total of costs to treat may be indicated in the form of a progress bar across a display. FIG. 3 illustrates display 300, which may show information 302 associated with a patient's electronic medical record (EMR) and a progress bar 304 of a health value continuum 301. Progress bar 304 may be shown on the display 300 along with the information 302 in the patient's EMR after the health care provider logs into the system 100. In some embodiments, as disclosed herein, the progress bar 304 the processing device 204 (see FIG. 2) may execute machine instructions to position the progress bar 304 immediately adjacent to, or near, the information 302. In some embodiments, the progress bar 304 is a horizontally oriented flood bar and extends across most or all the display 300 from the left side to the right side. In some embodiments, as the progress bar 304 "fills" from the left to the right, the progress bar 304 changes color regions, going from green region 304a on the left to yellow region 304b in the middle and red region 340c on the right.

The progress bar 304 may represent activity related to value continuum 301. A left (green) end of the progress bar 304 may be associated with zero cost (i.e., little or no activity related to the value continuum 301). The right (red) end of the progress bar 304 may represent the expected reimbursement or baseline cost to treat for the medical procedure. In effect, then, the progress bar represents progress toward reaching an expected reimbursement or baseline cost to treat for the medical procedure (as disclosed herein, the expected reimbursement or baseline cost to treat, and hence the progress bar 304 and value continuum 301, may increase (or in some cases decrease) during a patient's visit). The green region 304a indicates that the aggregated costs of care are within the expected reimbursement or baseline cost window, and may be referred as "high value" or "premium value." The yellow region 304b may indicate that costs are starting to approach or exceed expected reimbursement or baseline cost to treat (referred to as "moderate value"). The red region 304c may indicate that costs are exceeding expected reimbursement or baseline cost to treat, and the care may no longer be good value (referred to as "low value"). Thus, a typical patient treatment plan may conclude with the aggregated costs approximately in the center of the yellow region 304b.

Each time a cost is added for the patient, the progress bar 304 may be updated to reflect the additional aggregated cost. For example, when a physician orders an antibiotic for a patient, the costs associated with that care are determined, and the effect of those costs relative to the overall reimbursement or average cost to treat may be indicated in real-time (i.e., as quickly as the processing device 204 executes machine instructions) by a change in the fill level (shown in FIG. 3 as edge 304') of the progress bar 304 on the display 300. For example, the edge 304' of the progress bar 304 may extend further to the right (thereby resulting in a longer bar), and the color of the progress bar 304 may shift from green to yellow or from yellow to red. This change in the progress bar appearance may apply for all aggregated costs, including pharmacy, nursing, physical therapy, x-ray/imaging, bloodwork, and the like.

FIG. 4A illustrates another example display 400 with another example value continuum 401 and progress bar 404 that may be used in the system 100. In an aspect, the displayed progress bar 404 may represent a comparison of a value baseline and the value continuum. The progress bar 404 may be displayed at the top of an EMR system display (e.g., the display 302 of FIG. 3) after the health care provider logs into the EMR. (The mechanics for displaying the value continuum and associated progress bar 404 are disclosed herein, including with respect to the descriptions of FIGS. 5A-11D.) In some embodiments, the progress bar 404 is integrated into (and is a part of) the EMR system display. In some embodiments, the progress bar 404 only appears after a diagnosis is entered into the EMR system.

As shown in FIG. 4A, the progress bar 404 includes three regions: a green region 404a, a yellow region 404b, and a red region 404c. The progress bar 404 also includes an indicator 406 that represents a current cost level on the progress bar 404. These regions 404a-404c may be similar to the green, yellow, and red regions of the progress bar 304 in FIG. 3. The background of the progress bar 404 may be scaled automatically based on the diagnosis. That is, the relative scale of each region 404a-404c and the cost thresholds associated with each region 404a-404c may be determined based on the diagnosis. For example, for one DRG (e.g., pneumonia), the transition from the green region 404a to the yellow region 404b might be associated with $6200 of aggregated costs, and the transition from the yellow region 404b to the red region 404c might be associated with $8100 of aggregated costs; for another DRG (e.g., heart surgery), the transition from the green region 404a to the yellow region 404b might be associated with $84,000 of aggregated costs, and the transition from the yellow region 404b to the red region 404c might be associated with $95,000 of aggregated costs.

In some embodiments, different aggregated or projected costs may affect the movement of the indicator 406 on the progress bar 404 at different times. For example, orders (e.g., cardiology, laboratory, medications, therapy consults, radiology, etc.) entered through a computerized physician order entry (CPOE) system (see for example, FIG. 5A) may register as costs immediately, thereby causing movement of the indicator 406 to the right on the progress bar 404. As another example, scheduled procedures may register as costs on the progress bar 404 when the procedure is scheduled. As still another example, room costs may update the position of the indicator 406 on the progress bar 404 at a designated time of day, e.g., at midnight when the system 100 updates room charges.

While the physician charges and costs are accrued and billed separately, facility charges and costs are typically a direct result of physician orders. These facility charges may include:

Room (base on room type, such as private or semi-private rooms, ICU, CCU, and other)—number of nights in each room type.
Pharmacy—general, supplies, IV solutions, and other.
Pharmacy administration.
Medications requiring specific identification and requiring detailed coding.
Medical and Surgical Supplies—general devices, such as oxygen, IV solutions.
Medical and Surgical Supplies—sterile devices.
Laboratory costs—chemistry, bacteriology and microbiology, and hematology.
Operating room procedures—separate from the physician charges.
Radiology—X-ray, CAT scans, other diagnostic equipment.
Transport.
Consults.

The comparison with the expected reimbursement or baseline cost to treat may account for different financial factors, including profit margins, "fudge factors", differences between insurance providers, seasonal variations of costs, and the like. For example, if a baseline cost to treat a particular diagnosis is $5000, but it is known that certain costs increase by approximately 10% during a particular time of year, the baseline cost to treat may be adjusted to $5500 before it is used as the target in the progress bar 404. Such adjustments may be made in a cost database, e.g., by a facility accountant or system administrator.

In some embodiments, the progress bar 404 may reflect an anticipated cost at discharge. The anticipated cost at discharge may be determined based on a number of factors, such as how long the patient has been admitted, the DRG, ICD-9 or ICD-10 codes, the costs aggregated up to a current time, and the like. Once determined, the anticipated cost at discharge may be displayed on or with the progress bar 404. The anticipated cost at discharge may serve as a "look ahead" feature that allows a health care provider to compare a patient's current costs against cost trends from similar patients to show how the patient's current costs are tracking.

FIG. 4B illustrates yet another example display with yet another example value continuum and progress bar that may be used in the system 100. In FIG. 4B, display 420 includes value continuum 421 and progress bar 424. In an aspect, the displayed progress bar 424 may represent a comparison of a value baseline and the value continuum. The progress bar 424 may be displayed adjacent to (e.g., at the top of) an EMR system display (e.g., the display 302 Of FIG. 3) after the health care provider logs into the EMR. The display 420 provides an indication 428 of costs-to-date and an indication 426 of the baseline cost to treat, which is derived from a probability distribution generated from historical cost values for a specific DRG or multiple DRGs. The display 420 also includes indications 429 of computed standard deviation values of the costs to treat for the specific DRG or multiple DRGs. The indications 429 may be expanded as one or two (or more) standard deviations or a fraction of a standard deviation.

In an aspect of the embodiment of FIG. 4B, the displayed data may include a baseline length (e.g., a mean or median value) of a visit and the standard deviation of visit length for the specific DRG or multiple DRGs. A baseline length of visit data may be presented on the display 420 in proximity to the progress bar 424. The displayed baseline length of visit for a DRG may be used by the health care provider, along with the progress bar 424, to help the health care provider plan the patient care. For example, the baseline length of visit gives the health care provider an estimated endpoint of care, so that the health care provider may start to generate a discharge plan, consider or schedule resources (rooms, nurses, etc.), and the like. Also, the baseline length of a visit may influence the health care provider's decisions on care. For example, if a baseline length of a visit for a particular diagnosis is three nights with a standard deviation of one night, and a particular health care provider regularly keeps patients with the same diagnosis for five nights, the health care provider may consider a change to his plan of care if the health care provider sees on the display 420 that the baseline visit length is three nights and his standard care plan is two standard deviations from the baseline.

In another aspect of the embodiment of FIG. 4B, display 420 also may, when alternate treatments are available for a specific DRG or multiple DRGs, provide a frequency display (not shown) for use of each alternate treatment in proximity to the progress bar 424. The frequency data may be derived from historical values.

The system 100 may be used for cost comparisons of alternate treatment plans. For example, if a patient experiences respiratory problems while in the hospital, the health care provider may determine that an x-ray or computerized axial tomography (CAT) scan is needed. The health care provider may provisionally enter an order for an x-ray on the display 420 and then view the movement of the progress bar 424 to see how the x-ray affects the overall value continuum. The health care provider may then provisionally enter an order for a CAT scan and then view the movement of the progress bar 424 to see how the CAT scan affects the overall value continuum. Because the cost of a CAT scan is so much higher than the cost of an x-ray, it is likely that the progress bar 424 would move closer to red due to the CAT scan than it would due to an x-ray. By comparing the movement of the progress bar 424 for each test before the test is ordered, the health care provider may better understand the financial effect of each test or order on the patient's treatment plan.

The system 100 also may be used in early decision making by the health care provider. Consider that a health care provider creates an order that may have some cost variability. For example, an order for physical therapy may have widely varying costs, depending on the number of sessions, the progress of the therapy, the condition of the patient, and the like. In some embodiments, the system 100 may be configured to display an estimated reimbursement or a baseline cost for the order based on the diagnosis before the order is finalized. The estimated reimbursement or baseline cost may be displayed in the system 100 in real time while the order is being filled to give the health care provider an indication of what an order will cost. The health care provider then may use those estimates in his decision making. As the order is filled and actual costs are incurred, the costs may be compared to the estimated reimbursement or baselinecost. In some embodiments, the actual costs also may be used to update the estimate for later procedures. Scheduled procedures may be handled in a similar manner. The cost for a scheduled procedure may be estimated at the time the procedure is scheduled based on a historical cost to perform the procedure on patients with the same diagnosis. In situations where a DRG is not available, ICD-9 or ICD-10 codes may be used, or an estimated cost for a procedure may be determined based on costs for the procedure across an entire patient population or the cost for the physician performing the procedure based on having performed the same procedure in the past.

In some embodiments, the process and metrics will be driven by the physician, since the physician is the health care provider who admits patients. The physician may have an overall value metric assigned to him. The overall value metric may be based on an aggregation of overall value continuums for a plurality (e.g., some, most, or all) of the medical visits, procedures, or diagnoses for which the physician is the attending health care provider. In other embodiments, health care providers other than a physician may admit the patient.

A specialist health care provider who provides services during a procedure (e.g., an anesthesiologist during a surgery) may bill separately for his professional services; thus, the fee for the specialist may not be included in the overall value continuum for a procedure. However, the resources of the facility that are used by the specialist may affect the overall value continuum. For example, one anesthesiologist may require multiple attempts to intubate, or may keep patients on a ventilator longer than other anesthesiologists, or may use more expensive anesthesia or in greater quantities than other anesthesiologists. Those costs will be incurred by the facility and will affect the overall value continuum for that procedure.

In some embodiments, consultations with other health care providers (e.g., other physicians, such as specialists) may be included in the determination of value, as shown in the value continuum and corresponding progress bar 424. Each health care provider may have an overall value metric assigned to him. When a health care provider in charge prepares to consult another health care provider, the health care provider in charge may review the overall value metric associated with the consultant to determine if the consultant represents a good value. By examining value metrics for multiple consultants, the health care provider in charge may determine which consultant represents the best value.

The system 100 may include one or more reporting applications or modules for reporting on value continuums. Reporting may be available to determine an overall value of each cost center (e.g., pharmacy, nurse, physician, caregiver in charge, consultant caregiver, lab, and the like) based on different parameters. The data in the reports may be grouped for a particular period; for a particular type of procedure, hospitalization, or diagnosis; for a particular clinic or hospital in a multi-facility hospital chain; or for any other parameter or combination of parameters. For example, reporting features may allow a user to review the overall value for all internal medicine physicians who treated pneumonia between March and September at Hospital A. The data may be broken out by physician or the data may be grouped for the physician group. Grouped data may be selected and a "drill-down" option may be applied to see more specific data. For example, grouped data may show that a physician has a value metric for a six-month period for pneumonia patients. However, a drill down on the grouped data may indicate that the physician had high value for all patients in the six-month period except for one patient with special circumstances, which lowered the physician's value metric. Trend reporting allows a user to review the value of a physician or other care provider at different points in time over a period.

Figure 5A:
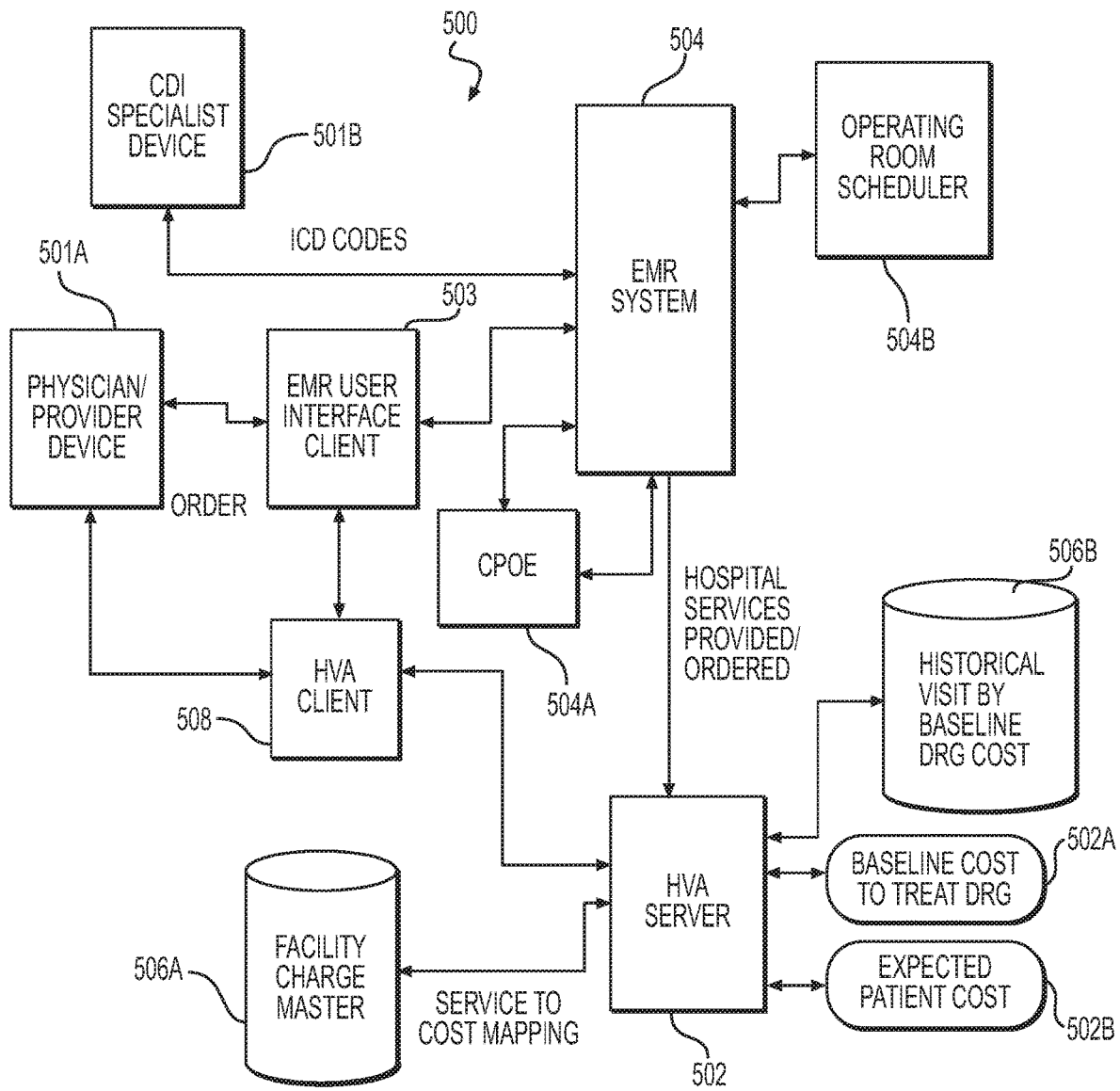
FIGS. 5A-5F illustrate other example systems, and components thereof, for determining and indicating value of health care.
Figure 10A:
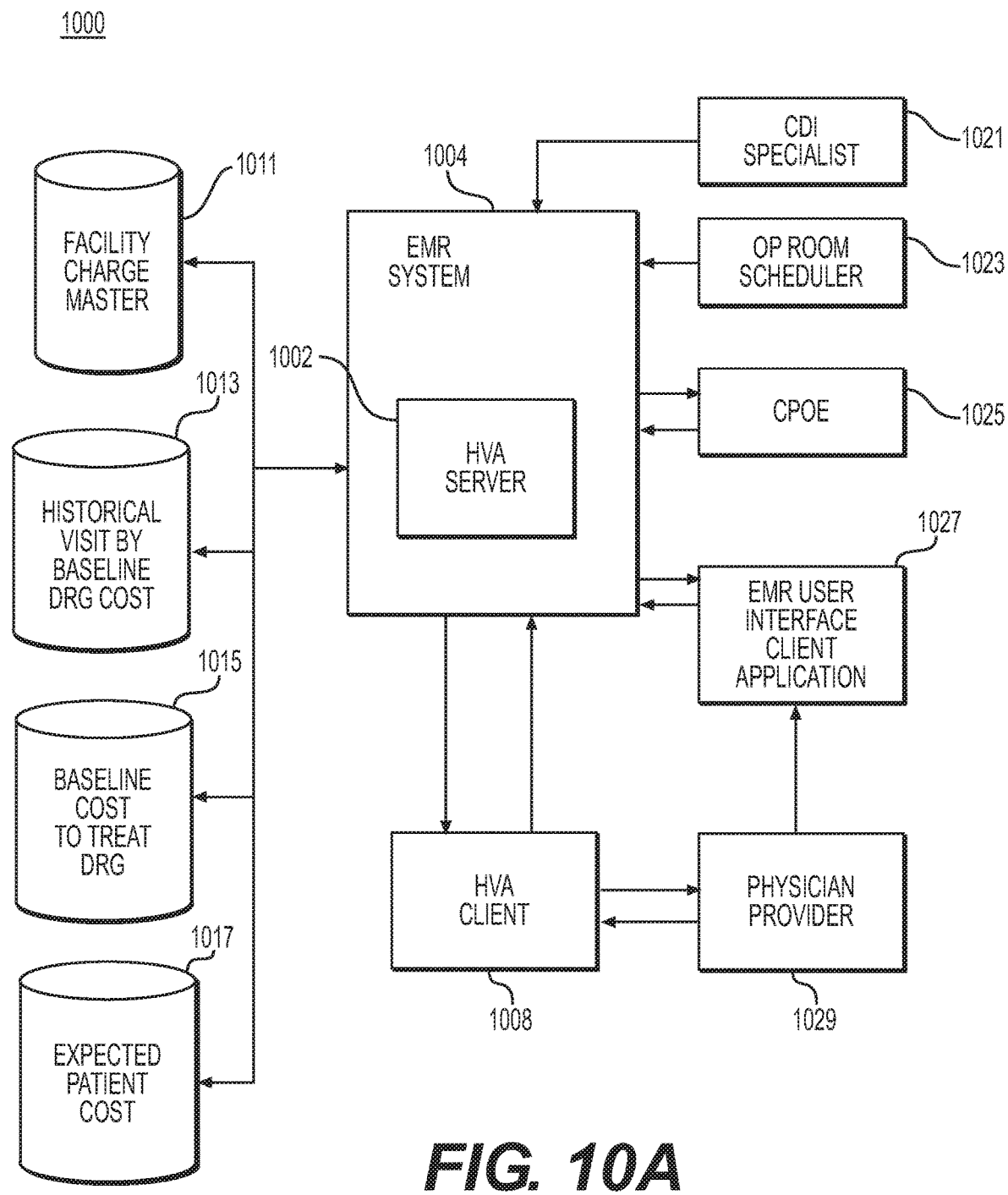
FIGS. 10A-10C illustrate other example systems for determining and indicating value of health care.
Figure 10B:
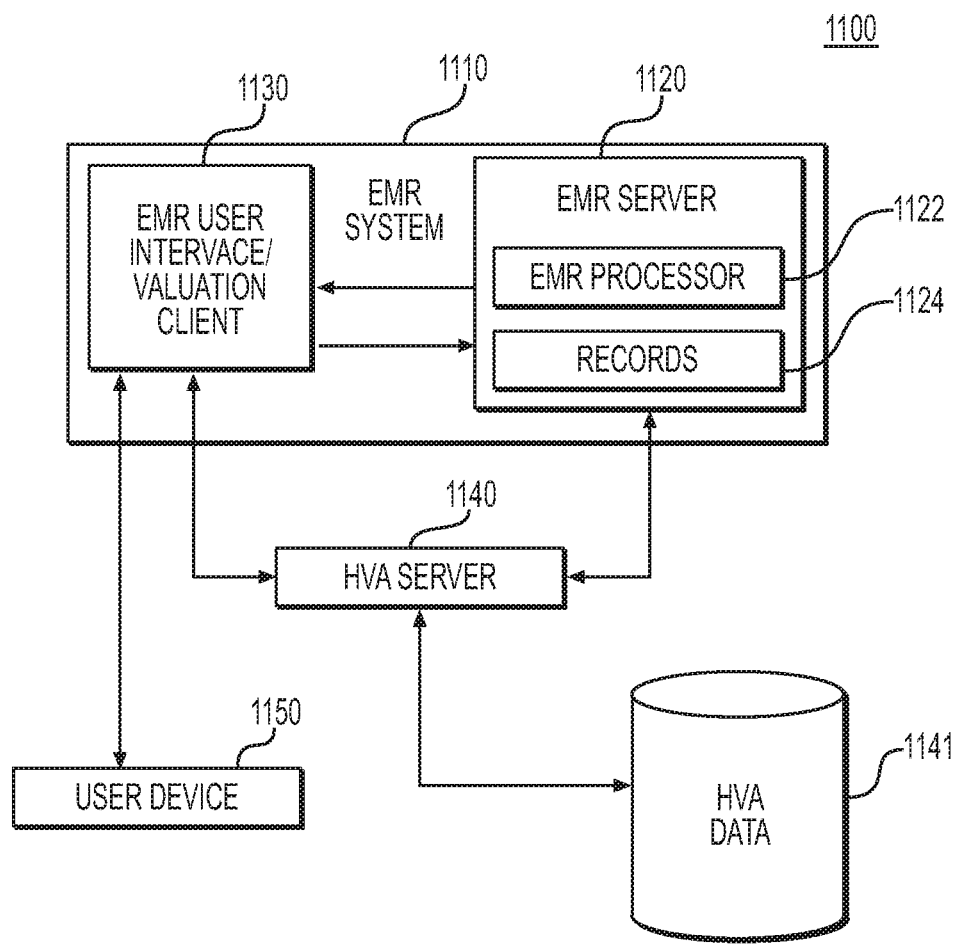
Figure 10C:
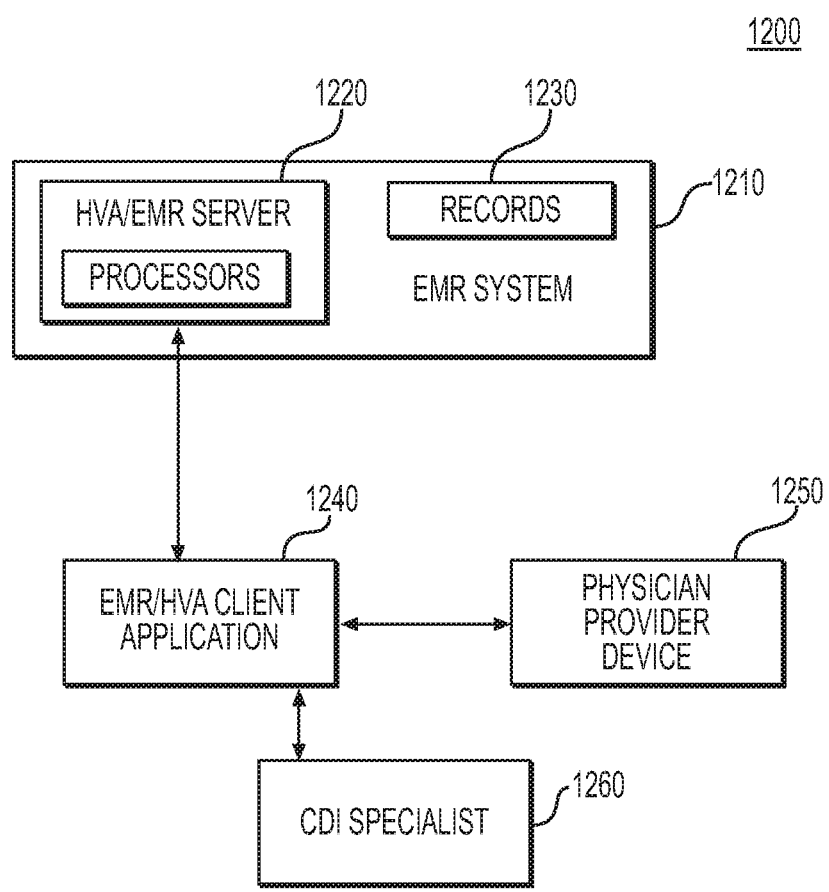

FIG. 5A illustrates example system 500 for determining and indicating value of health care. One or more components of the system 500 may correspond to one or more components of the system 100 of FIG. 1. The system 500 includes a Health Value Analytics (HVA) server 502, an electronic medical record (EMR) system 504, a facility charge master data source 506A, and one or more HVA clients 508. The EMR system 504 includes a server and records store (not shown). The system 500 further includes computerized physician order entry (CPOE) module 504A, operating room scheduler 504B, EMR user interface client 503, and data source 506B (historical visit by baseline DRG cost). The HVA server 502 produces baseline cost to treat DRG 502A and expected patient cost 502B. The EMR system 504 may be accessed and used by health care providers such as a physician provider at physician provider device 501A, and hospital staff, such as a CDI specialist, at CDI device 501B. In an embodiment, a physician provider or CDI specialist may access the devices 501A and 501B, respectively, using, for example, a personal data assistant or other devices such as the end user devices 104-110 of FIG. 1 through a virtual private network (VPN) (not shown). In an embodiment, some components of system 500 may be software programs instantiated on system 500 hardware components. For example, COPE module 504A and the EMR user interface 503 may be software modules resident on hardware devices of the EMR system 504. In this example, a physician may access EMR user interface client 503 and invoke CPOE module 504A to enter patient orders. In an embodiment, the components of the system 500 may be behind a firewall such that communications between and among the components are simplified, and communications security is enhanced. In an aspect, the EMR system 504, devices 501A and 501B, CPOE 504A and operating room scheduler 504B, and EMR user interface client 503 may be components of a legacy hospital system while the HVA server 502 and HVA client 508, and associated data stores 502A, B, and 506A, B, may be added to, integrated with, or simply in communication with the legacy hospital system. FIGS. 10A-10C provide alternate arrangements of the components of FIG. 5A.

The HVA server 502 may be a back-end server (similar to the server 112 of FIG. 1) that connects (via a network connection) to the EMR system 504 for the hospital system or group where the system 500 is installed. The system 500 may integrate any EMR system, such as the EMR system 504, with the HVA server 502 and its related components. In some embodiments, sensitive patient or provider information, such as names, addresses, phone numbers, Social Security numbers, and personal credit card numbers or other financial data, is not stored in the HVA server 502. In some embodiments, the HVA server 502 receives order information, patient information, and the like from the EMR system 504 by executing data search commands to retrieve the information from the EMR system 504 database. In other embodiments, the HVA server 502 receives order information, patient information, and the like from the EMR system 504 by, for example, an HL7 (Health Level 7) interface (not shown) to the EMR system 504.

The facility charge master data source 506A is a database, data table, or other data source that includes charge information for a hospital or other facility. The HVA server 502 stores or is able to access the charge information from the facility charge master data source 506A, and uses the information from the data source 506A to convert orders received from the EMR system 504 to one or more costs. In some embodiments, the facility charge master data source 506A may be received by the HVA server 502 as a file (e.g., via email). The file then may be loaded into the HVA server 502. Alternately, the HVA server 502 may connect directly to the hospital or facility accounting system (not shown) to retrieve these charges. Ultimately, it is hospital or facility costs that are used in the system 500; these may be determined simply by multiplying a cost-to-charge ratio factor by the charges or have a table or method of calculating costs from the orders.

The EMR user interface client 503 may be implemented as software or hardware. In an aspect, the EMR user interface client 503 is accessed by physician provider device 501A to connect to the EMR system 504. The physician provider device 501A may be used to access the HVA server 502 by way of the HVA client 508.

The HVA server 502 may connect to a hospital or facility contracting system to obtain accurate cost estimates based upon admitting diagnosis codes or DRG codes when they become available. Alternatively, the HVA server 502 may calculate the cost data itself, either from a statistical model fit to historical data or from a DRG cost calculator. If the HVA server 502 performs the calculations, factors, rates, and formulae may be stored in the HVA server 502 for easy access. If a statistical model is used, then the HVA server 502 may act upon patient symptoms or diagnosis codes for input to the model.

The HVA server 502 may be configured with one or more data stores for use by the system 500 to support model development and displays. Such data that the system 500 supports include:

A range of DRG reimbursement amounts based on diagnoses, including blended rate multipliers, and other factors.

Facility costs associated with any order that is possible for a patient. Historical data may be maintained within the system 500 for model development, and data may be continually, periodically, or episodically updated to provide the most recent costs pertaining to the physician orders. These costs include: supplies (drugs, IV fluids, oxygen, and the like), producing X-rays, CAT scans, and lab work, cost of nursing care, and room charges with time increments for all types of rooms.

Any data from a facility accounting system (not shown) that may help with actual reimbursements, order costs and schedule costs.

Each HVA client 508 may be accessed on a client device or end-user device with a display (such as one of the end user devices 104-110 of FIG. 1) and provides functionality for users of the system 500 to view the health care value continuum. Each HVA client 508 may exchange information with the HVA server 502 over a secure network link via one or more custom APIs.

Each HVA client 508 may be installed on a client device (such as one of the end user devices 104-110 of FIG. 1) as a stand-alone application or as a plug-in. Alternately, each HVA client 508 may reside on another central device (e.g., the HVA server 502) and be accessed by a client device.

Figure 5B:
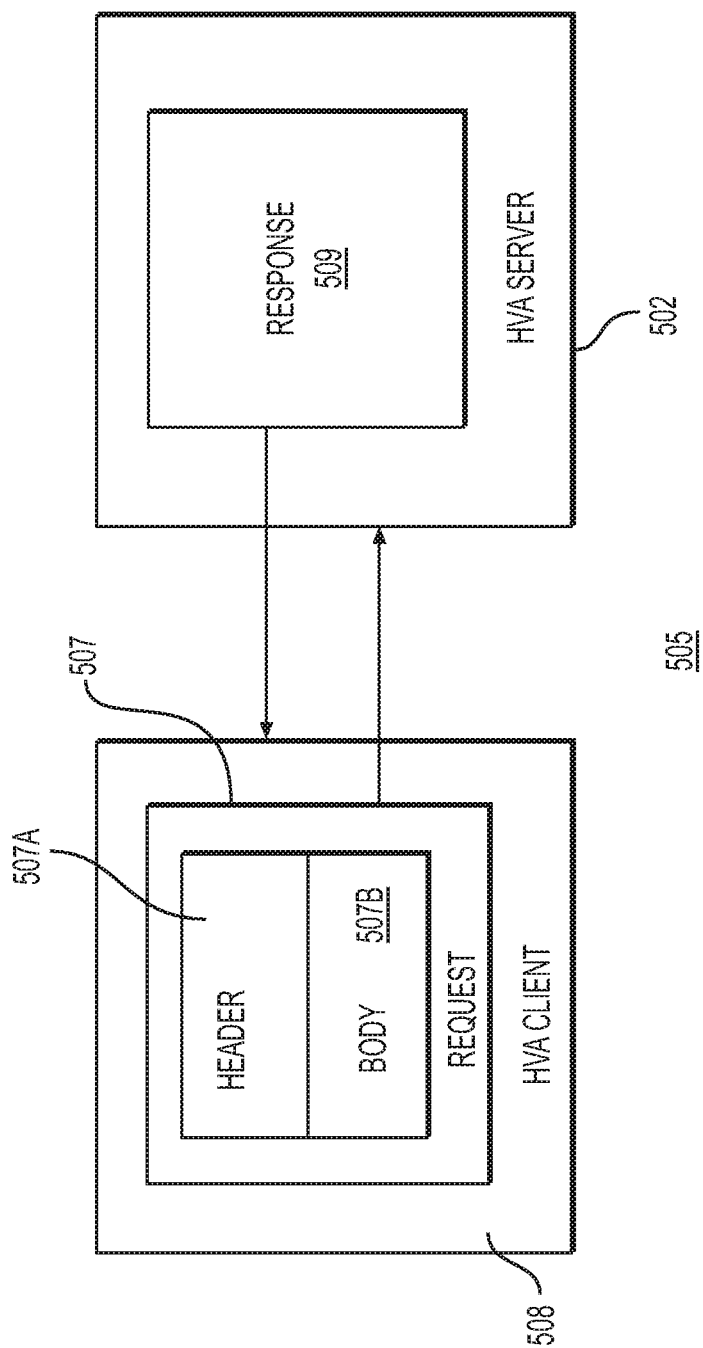

In an embodiment, the HVA client 508 and the HVA server 502 communicate using architecture 505, a part of which is shown logically in FIG. 5B. The HVA client 508 may make many requests 507 to HVA server 502. A request 507 from the HVA client 508 to the HVA server 502 includes (i.e., within the request itself) the necessary information to allow the HVA server 502 to respond properly to the request 507. After the HVA server 502 has completed its processing, the appropriate information is communicated back to the HVA client 508 in response 509. The request 507 is seen to include a header 507A as well as a body 507B. The necessary information may be contained within the header 507A. The header 507A uniquely identifies the source (HVA client 508) and the state, or state change, of the HVA client 508. Using the architecture 505, the HVA client 508 and HVA server 502 may establish a session having a specific Session ID, and the Session ID may persist and be used to automatically reconnect the HVA client 508 and HVA server 502 as needed. HVA client 508

Figure 5C:
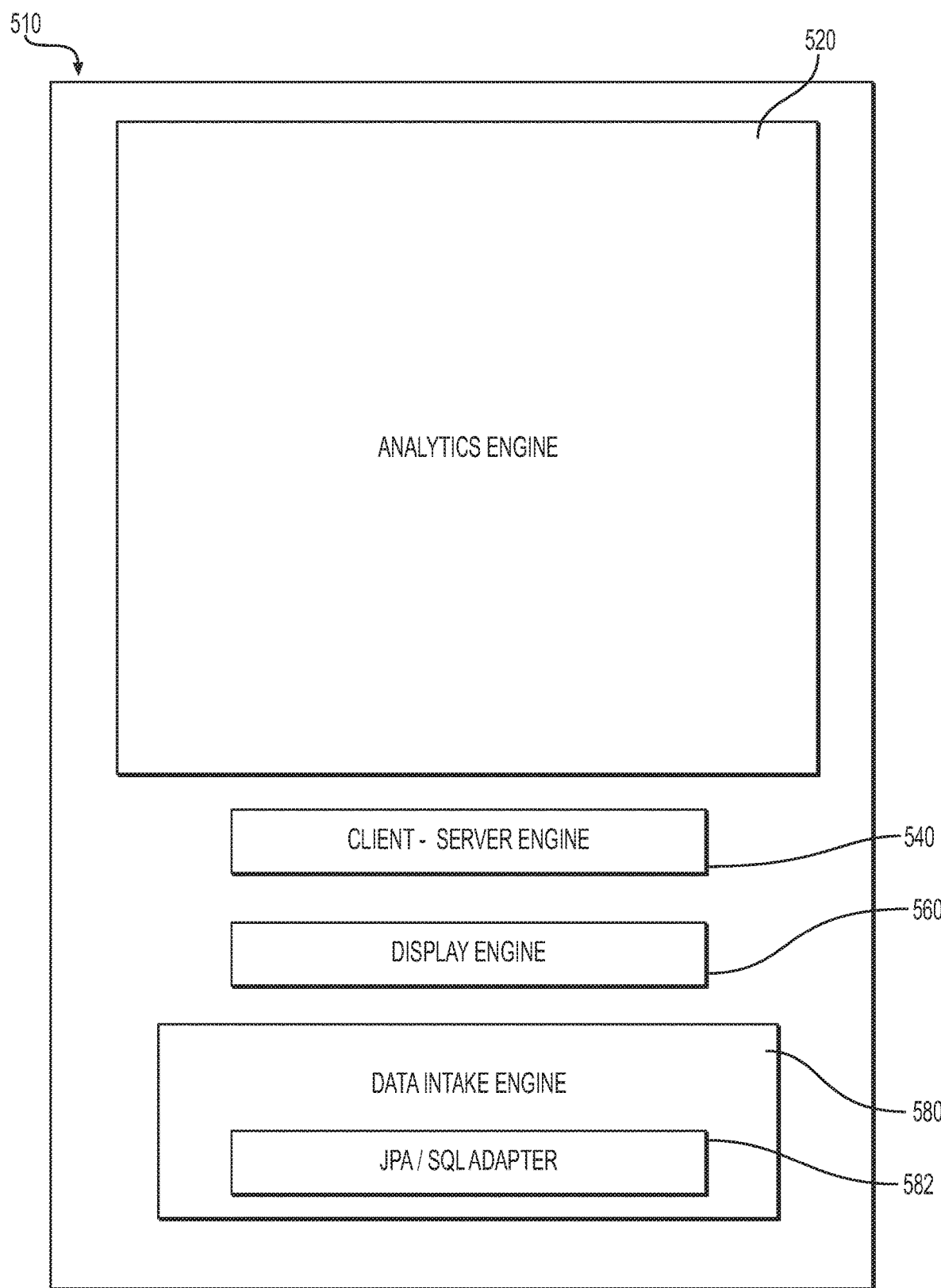

FIG. 5C illustrates an example program of instructions executable by processors resident in or accessible by the HVA client 508 and the HVA server 502. In FIG. 5C, program 510 includes components that may be distributed between and among HVA clients 508, the HVA server 502, and other workstations and processing and data storage devices, including those shown in the example system 500 of FIG. 5A. Moreover, the example program 510 shown in FIG. 5C is for illustration purposes, and the various components of the program 510 may be combined or separated. The program 510 includes analytics engine 520, client-server engine 540, display engine 560, and data intake engine 580. The analytics engine 520 includes analytics models and cost models. The client-server engine 540, in an embodiment, employs the stateless transfer architecture 505 of FIG. 5B to allow efficient, accurate communications (requests and responses) between the HVA client 508 and the HVA server 502. The client-server engine 540 is shown in more detail in FIG. 5D. The display engine 560 includes display drivers to display the progress bar and other data.

The HVA server 502, in cooperation with the HVA client 508, and other components of the system 500 of FIG. 5A, executes components of the program 510 to display interfaces such as the displays of FIGS. 3, 4A, 4B, and 8A-8C.

The HVA Server 502 also executes the program 510 to develop or use specific models, to populate specific data stores, to analyze data using the models, and to interact with the HVA client 508 and the EMR system 504. For example, the program 510 is executed to compute Measured Cost, which is a cost basis used to compare against a Baseline Cost. The Baseline Cost is derived from application of analytics models and cost models and various methods of the analytics engine 520. For example, an estimate and correct method may be used to derive the Measured Cost, such that any time actual costs to treat a patient exceed estimated costs to treat the patient, the actual cost to treat the patient is used in lieu of the estimated cost to treat according to: Measured Cost=max (Sum(Orders), Sum(Actuals)). To derive Sum(Orders) for every ordered/scheduled event the, the analytics engine 520 may be accessed to apply the following logic: for events that have a cost based on variables not known at the time of order, the cost will be estimated using a method defined in the analytics engine 520 (baseline cost from the analytics models) to approximate the following variables: Procedures: the measured cost=max (estimate for procedure, actuals for procedure); Therapies: the measured cost=estimated for therapies; Quantities (PRN): assume quantity=1; and Time: the maximum time duration is assumed. Total Cost is derived by comparing the Measured Cost against the Benchmark Cost for the diagnosis. Predicted Cost is derived by comparing the Measured Cost against the Expected Costs (from the analytics models) for the diagnosis and current length of treatment. Category Cost Totals are derived from partitioning the Measured Cost using a defined mapping based on revenue codes (from the analytics models: for example, Radiology, Lab, Procedure, Therapy, Pharma, Room, Other). Order Totals are derived from partitioning (disambiguating) the Measured Cost using charge codes and including a frequency metric (from the analytics models) for the diagnosis. In an example, the HVA Cost Model has five components, which may be .csv files that have formats and use data specified as follows. charge_codes.csv; PharmaNDCCodeCosts.csv; ChargeCodeCosts.csv; DRGAdjustedAverageCosts.csv; and category_thresholds.csv. The first three files may be applied to charge codes that are assigned to individual patient visits, the DRGAdjustedAverageCosts.csv file is referred to as the Baseline Cost, from which savings may be compared. The category_thresholds.csv file partitions or disambiguates the Baseline Costs into seven individual categories by DRG: Room, Lab, Procedure, Pharma, Therapy, Radiology, and Other.

To build the Baseline Costs, the HVA analytics engine 520 may execute instructions of the data intake engine 580 to access data from the EMR system 504. For example, the HVA analytics engine 520 populates a number of tables in a local data store, including Populate the hospital_pharma_costs table. This process involves reading data directly from the EMR system 504. The first step involves running valuation program HVAAnalytics, which may be a .jar executable, for example) on the HVA analytics engine 520 using the flag: processARangeOfEMRIntakes=true to produce a very large file, PharmaExportData.csv. This very large file includes any corrections for pharma charge codes seen in the EMR database. This file may be exported and uploaded into the hospital_pharma_costs table using the command:

LOAD DATA INFILE '/disk2/ipx/Hospital/PharmaExportData.csv' INTO TABLE hospital_pharma_costs FIELDS TERMINATED BY ',' OPTIONALLY ENCLOSED BY " " IGNORE 1 LINES;

The next step is to populate hospital_pharma_intakes tables by executing the THCICDataAnalytics.jar program with the following flags: readInHospitalPatientIntakesData=true; readInHospitalCostToChargesData=true. Step 3: Populate the charge_code and pharma_NDC_code tables. This step is performed using the THCICDataAnalytics.jar program with the following flags: refreshChargeCodesFromDB=true; refreshPharmaCodesFromDB=true. When the program completes, the HVA analytics engine 520 dumps the contents of the charge_codes and pharma_NDC_code tables to comma-separated files: ChargeCodeCosts.csv and PharmaNDCCodeCosts.csv, respectively. The HVA analytics 520 does this by running SELECT*FROM charge_codes WHERE 1. The HVA analytics engine 520 uses a comma-separated file (.csv) format to export the results from this query to a flat file named ChargeCodeCosts.csv.

Figure 8A:
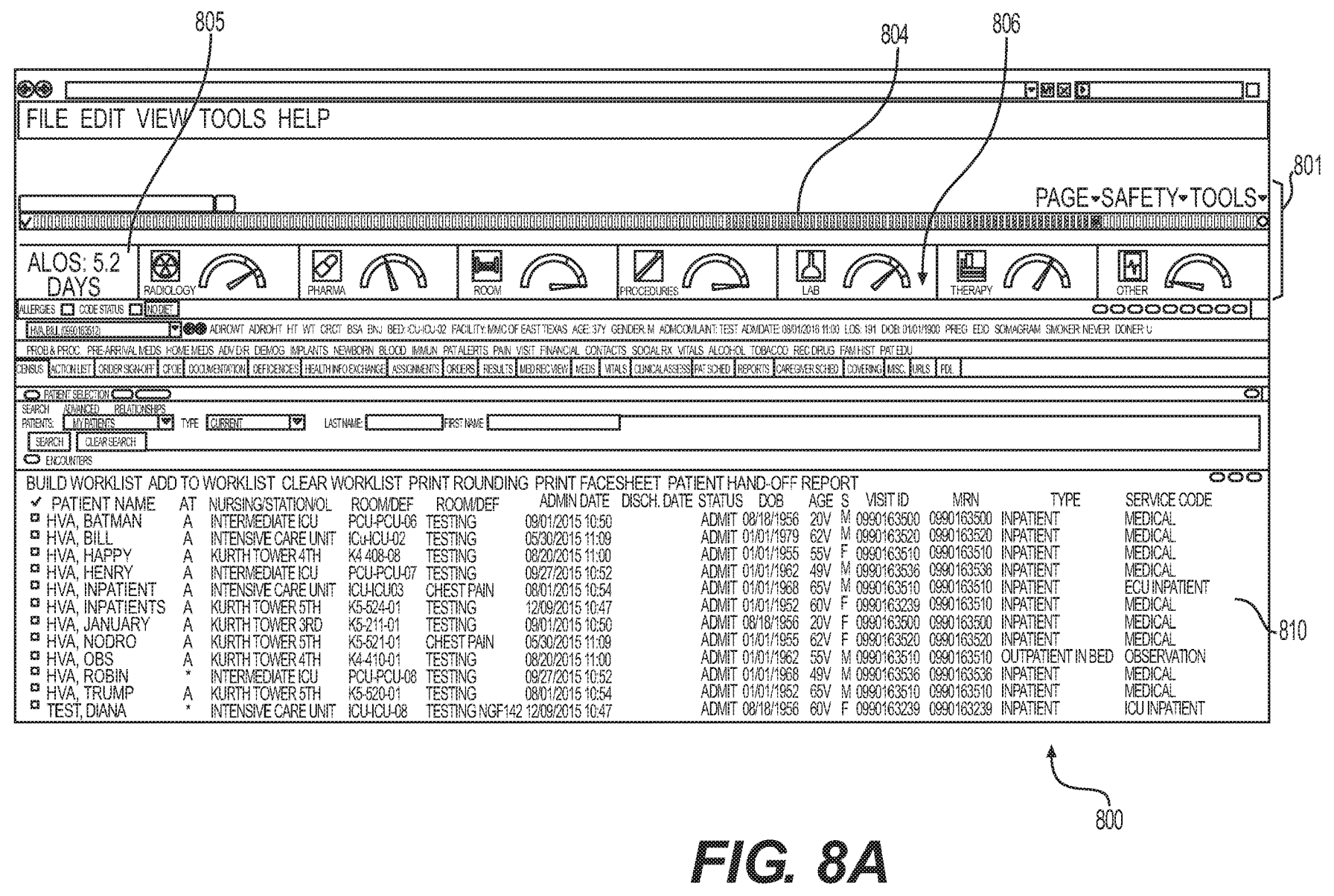
Figure 8B:
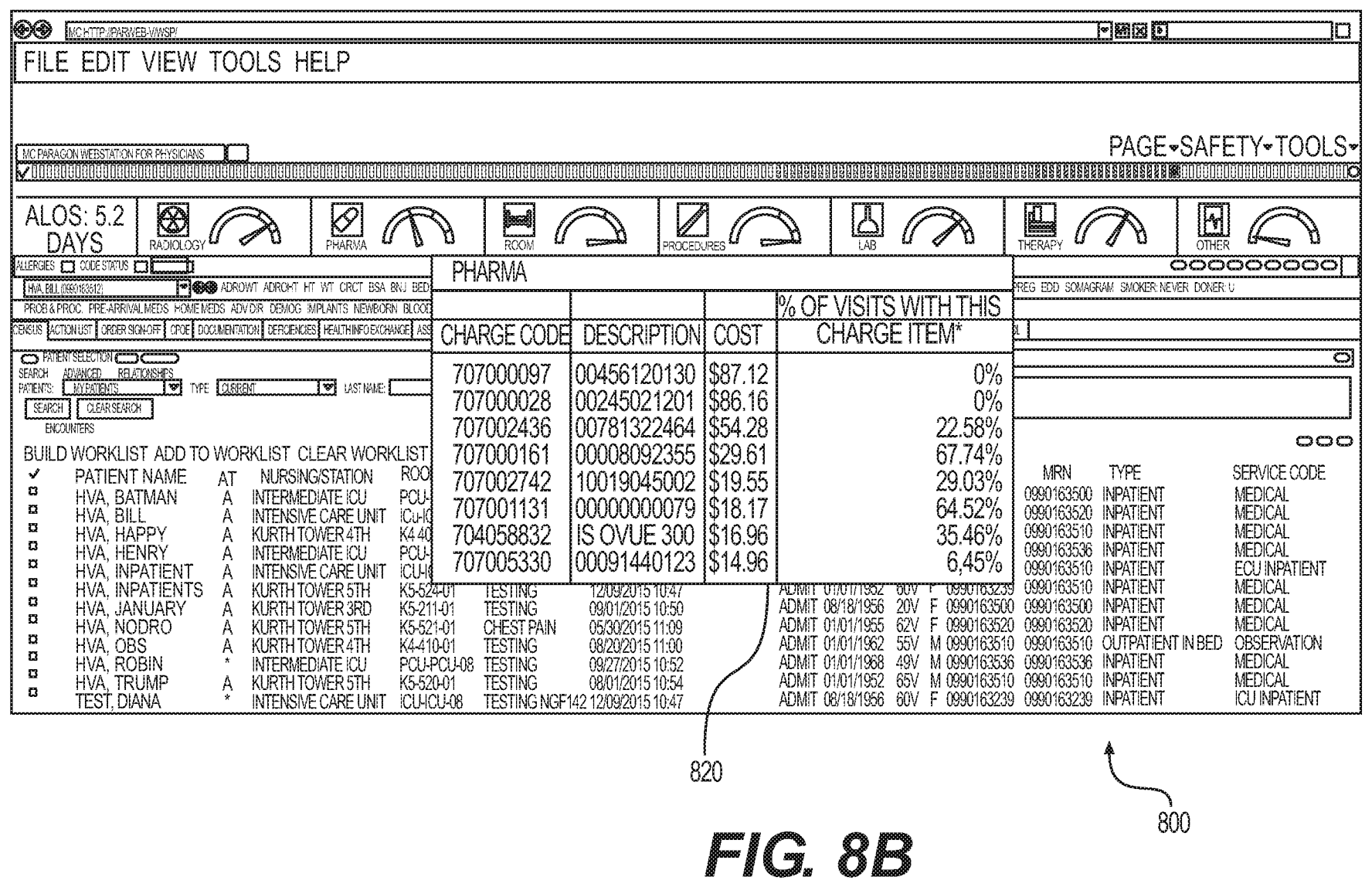
Figure 8C:
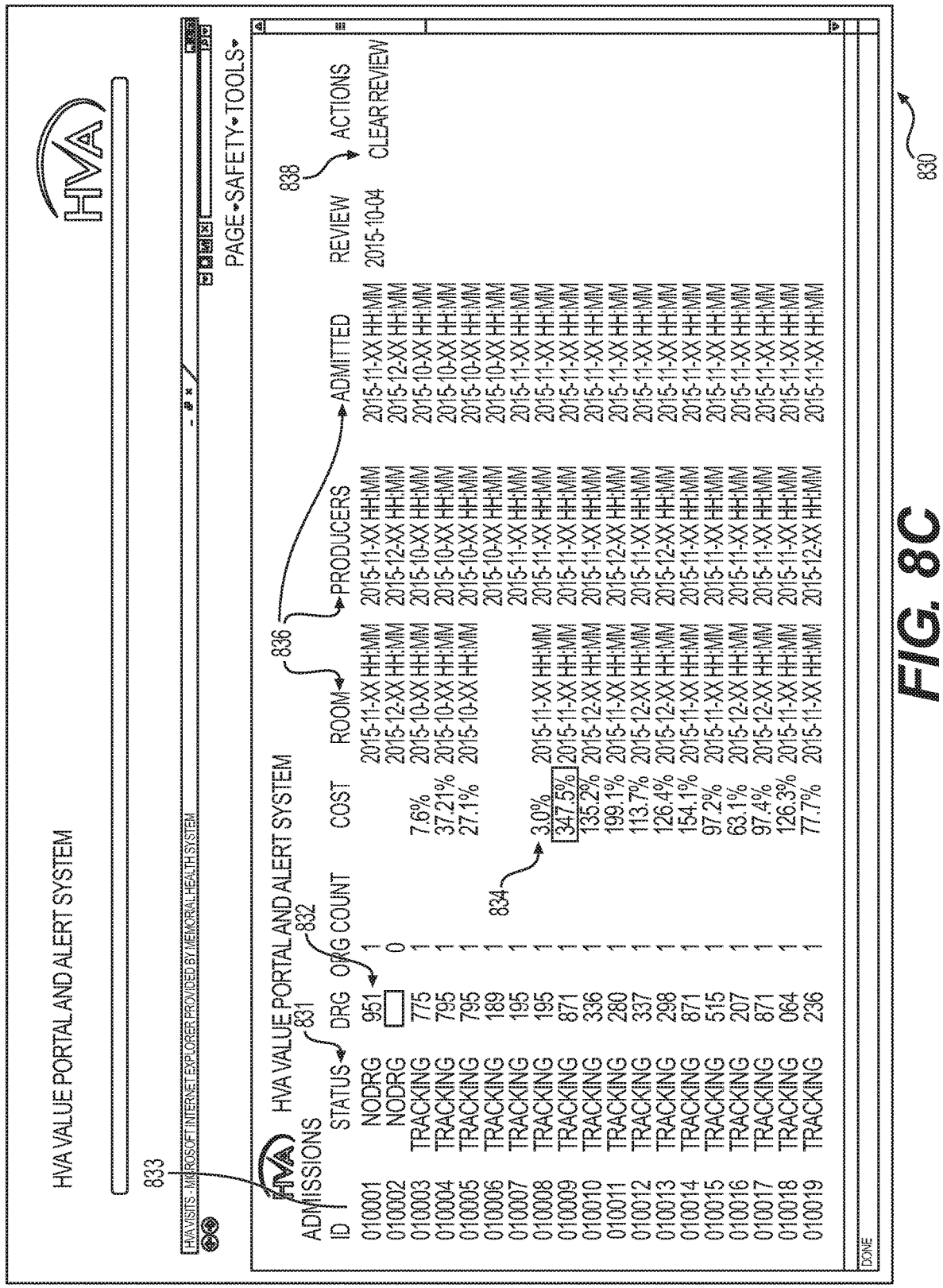

In an embodiment, the HVA client 508 enables a display that is the same as or similar to the display 300 of FIG. 3, the display 400 of FIG. 4A, the display 420 of FIG. 4B, or the displays of FIGS. 8A-8C. The displays may include one or more of the following features:

A progress bar (e.g., the progress bar 304, 404, 424, 804) that compares actual and scheduled costs aggregated by the hospital or facility against the baseline cost expected for care delivered or expected reimbursement based upon the admitting diagnosis or DRG codes. The progress bar may include three primary colors—Green means that the value of care is good and the estimated cost is less than the baseline costs based on the working DRG ("premium value," e.g., less than 85% of baseline cost), yellow indicates that costs are starting to approach or exceed baseline costs ("moderate value"), and red indicates that the value of care is poor with recognized cost overruns ("low value," e.g., at least 115% of baseline cost). In an aspect, rather than expressing thresholds as percentages of the baseline costs, the thresholds may be expressed in terms of standard deviations or fractions of a standard deviation.

Specific details that define how the progress bar is to be displayed including flood percentage and color information may be stored at the HVA server 502 and may be configurable by a user or a system administrator.

The user may click on or hover over the progress bar, which brings up additional information about the patient or about costs associated with the patient. The type of additional information that may be displayed includes but is not limited to:

Baseline length of visit

Aggregated cost of laboratory orders as compared to the baseline cost of laboratory orders Aggregated cost of radiology orders as compared to the baseline cost of radiology orders Aggregated cost for procedures as compared to the baseline cost of procedures Aggregated cost for medications ordered as compared to the baseline cost of medications ordered Aggregated cost of room charges as compared to the baseline cost of room charges Aggregated cost of therapy orders as compared to the baseline cost of therapy orders A detailed list of all the discrete orders and the associated costs for each order.

The type of additional information and the way the additional information appears are configurable by a user or a system administrator.

The HVA client 508 may interface with EMR system 504 or an order system that the physician uses to connect to the EMR system 504 (e.g., CPOE module 504A) as a patient's treatment plan is updated, so that real-time updates may be sent to and from the EMR system 504 and the user may see these updates at the HVA client 508 as the updates occur.

Information to populate the value continuum and the progress bar in the HVA client 508 is provided by the HVA server 502. Calculations and display information may be controlled at the HVA server 502 or may be performed by a client device.

Security features support secure access to the HVA client 508. For example, access to the HVA client 508 may be granted only after a user provides a suitable user ID and password. In some embodiments, a system administrator may access a security maintenance application on the HVA server 502 to provide authorization for a user to access the HVA client 508 and see content. Since the progress bar may be displayed as part of a patient EMR view, the HVA client 508 may infer user privileges based on corresponding user privileges in the EMR system 504. In some embodiments, the HVA client 508 will only display the value continuum and the corresponding progress bar if the user is a physician of record for the patient being viewed.

The system 500 operates in real-time or near real-time, such that changes to data in various components of the system 500 may be reflected in other components concurrently or within a short period after the change. For example, whenever data from the EMR system 504 for a patient record that is currently on display at the HVA client 508 is updated with new information relating to either the DRG or the orders/costs associated with the patient, the system 500 becomes aware of the data changes within a short period (e.g., 15 seconds) of the change and presents updated HVA value content on the display of the HVA client 508. Example mechanisms to "make the system 500 aware" are disclosed herein, including with respect to the description of FIG. 5D.

Components of the system 500 may monitor changes in the treatment plans by periodically comparing the latest measured values against the baselines. The components may use configurable threshold ranges to define notification events that may be sent to a subscribing endpoint (by, for example email, message queues). Example endpoints shown in the system 500 of FIG. 5A include an account of physician provider (who may access the account using the EMR user interface client 503).

To provide an alerting function (such as display 830 of FIG. 8C), value continuum updating in real time, and reduce bandwidth demand on the network of FIG. 5A (the network being the connections between and among the components of system 500, and in particular, the connections between and among the EMR user interface client 503, HVA client 508, HVA server 502, and EMR system 504), queries, requests, and demands on the EMR system 504 database, and general computational load on the EMR system 504, may be handled in such a way that some activity by a physician/healthcare professional (the physician provider) may be handled before the HVA client 508 is able to request an update to the value bar. In an aspect, the required "activity" may be an event such as clicking on the value bar, for example. Such activity may be detected by a thread listener and the resulting action may be invoked through operation of an thread handler. Example thread listeners and handlers are disclosed herein, for example, with respect to FIG. 5D.

Figure 5D:
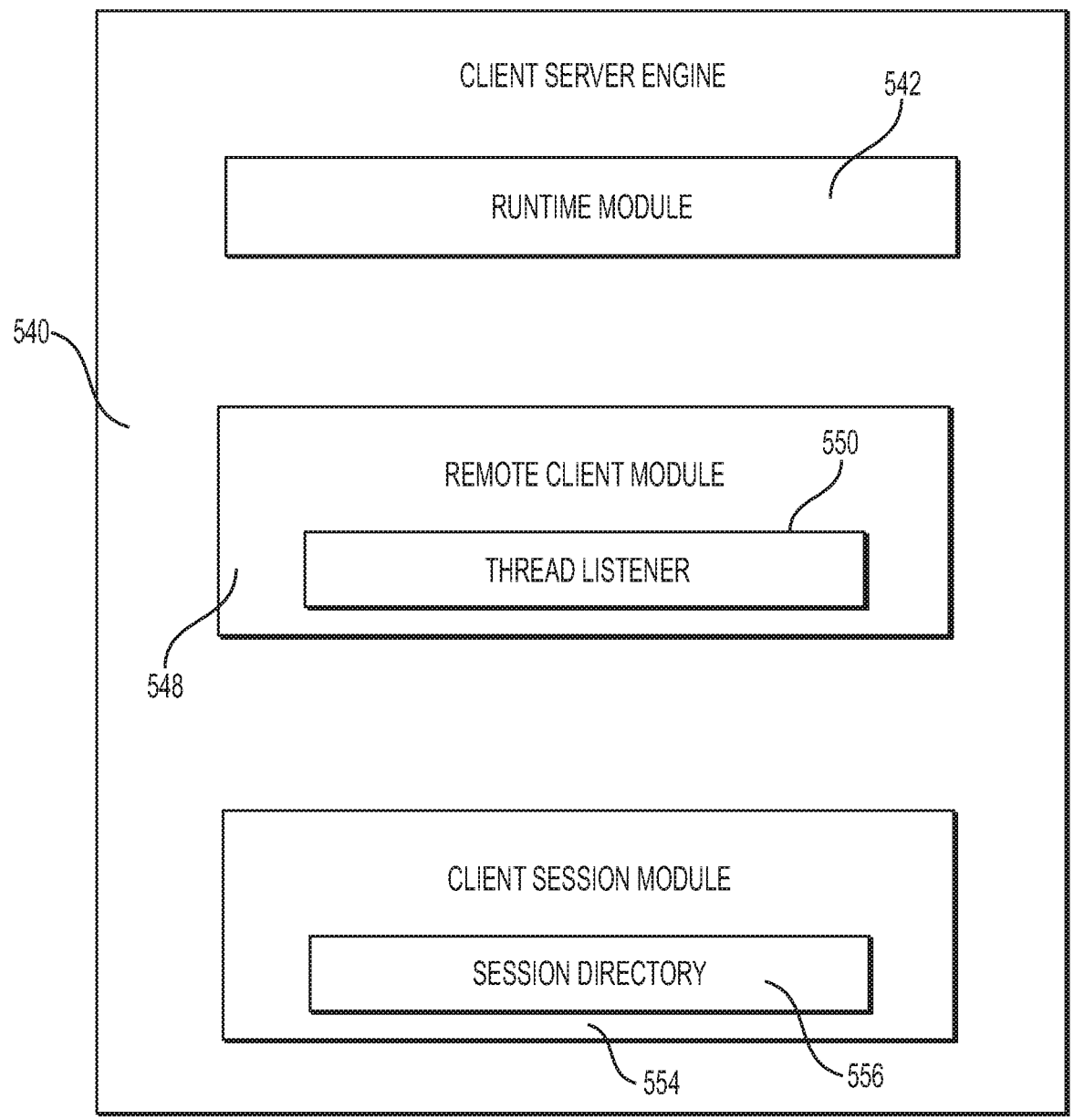

FIG. 5D illustrates an example client server engine 540. The client server engine 540 provides the ability to host multiple, simultaneous client sessions executing on both Windows®-based and non-Windows®-based hardware. Installation of the client server engine 540 provides HVA clients 508 access to applications running entirely on the HVA server 502, supports multiple client sessions on the HVA server 502, and provides application execution and data processing on the HVA server 502. As HVA clients 508 attempt to connect to the HVA server 502, the client server engine 540 detects the attempt and initiates a client session and subsequently, all application execution and data processing occur on the HVA server 502. The client server engine 540 includes client-server runtime module 542, remote client module 548, and client session module 554. The client-server runtime module 542 provides thread handling for all HVA clients 508. The remote client module 548 includes thread listener 550. The remote client module 548 captures the remote HVA client user interface and translates the user interface into a form that is compatible with the HVA server 502. The remote client module 548 also controls transfer of multi-channel data to the appropriate client session. The remote client module 548 cooperates with the client session module 554 to establish and maintain the connection between a HVA client 508 and the HVA server 502 executing the client server engine 540. The client session module 554 initiates all client sessions, and provides client connection services including reconnection and logoff. The client session module 554 initiates client sessions by listening to HVA client 508 connection requests at a TCP port of the HVA server 502. The client session module 554 also manages the session environment by receiving mouse and keyboard clicks from the HVA client 508 as inputs and sending the inputs to the appropriate application executing on the HVA server 502. The client session module 554 keeps a list of sessions indexed by user name, and allows a user (e.g., a physician health care provider) to reconnect to the HVA server 502 and resume a session. As the HVA server 502 boots and loads its core operating system, including the program 510, the client-server runtime module 542 service starts and begins waiting for session connections. Each connection is given a unique session identifier or Session ID to represent an individual session to the HVA server 502, and each process created within a session is tagged with the associated Session ID to differentiate the process from any other HVA client sessions. HVA client sessions are configured to load separate drivers for the display, keyboard, and mouse. These drivers allow the HVA client session to be both available and interactive, remotely. Finally, the remote client module 548 invokes a connection thread listener 550, which listens for client connections and inputs on a TCP port of the HVA server 502. At this point, the client server process exists with its own Session ID, with data instantiated per process as necessary. Any processes created from within this Session ID will execute within a session space of the client server process, automatically, thereby preventing processes with different Session IDs from accessing another session's data. Thus, in an aspect, the client server engine 540 provides remote access by the HVA client 508 to a the HVA server 502 through "thin client" software provided by the HVA server 502 to the HVA client 508, allowing the HVA client 508 to serve as a terminal emulator. A HVA client 508 may exist in a variety of forms. Thin-client hardware devices that run an embedded operating system may run the thin client software to connect to the HVA server 502. Windows®, Macintosh®, or UNIX® computers may run thin client software to connect to the HVA server 502 to display Windows®-based applications. A session directory component 556 of the client session module 554 maintains a list of sessions indexed by user name, and allows a user to reconnect to the HVA server 502 to resume a previously terminated session. The client server engine 540 transmits only the user interface of the program to the HVA client 508, with the HVA client 508 connecting through the local network, sending keystroke and mouse-movement information over the local network to the HVA server 502. The HVA client 508 then sends client screen information in the form of simple (and bandwidth-friendly) events, backed with bitmap information if required to properly display the client state. Each user logs on and sees only his individual HVA client session, which is managed transparently by the HVA server 502 operating system and is independent of any other HVA client session. The client server engine 540 provides virtual session management, so users can essentially treat a session as their own personal computer. The client software is a very small software application that establishes and maintains the connection between a HVA client 508 and the HVA server 502. Each HVA client 508 transmits all inputs from the user to the HVA server 502, such as keystrokes and mouse movements, and all output from the server such as application display information and print streams. The thread listener 550 detects the session request and creates a new stack instance to handle the new session request. The thread listener 550 hands over the incoming session to the new stack instance and continues listening on the TCP port for further connection attempts from other HVA clients 508 as well activity from the connected HVA client 508. The logon process performs the necessary account authentication to ensure that the user has sufficient credentials to log on and then passes the user's domain and user name to the HVA server 502, which maintains a domain/user name—Session ID list. If a user decides to disconnect the session, the processes and all virtual memory space remain and are paged off to a physical disk if memory is required for other processes. Because the HVA server 502 maintains a mapping of domain/user names and Session IDs, when the same user reconnects (regardless of which HVA client 508 the user controls), the previously-established session is loaded automatically and again is made available to the user. This automatic reconnection process adds resilience to the HVA client session and is designed to recover from temporary connection losses due to network problems. Automatic reconnection also enables disconnected client sessions to automatically re-authenticate to the HVA server 502 without prompting the user for credentials.

In one example execution of the client server engine 540, a physician provider using the device 501A may log in to the system 500 (i.e., may operate the EMR user interface client 503, access the CPOE module 504A, and enter an order for a newly-admitted patient). The client server engine 540, invoking thread listener 550, identifies the log-in and order entry as an activity that calls for creation of a value continuum and corresponding progress bar, and sends a request 507 to other components of the HVA server 502, which in turn execute instructions to create and display the value continuum and the corresponding progress bar. In a second example, when a link is clicked-on thread listener 550 detects the click on as an activity or event that may require recomputation of the cost to treat that is reflected in the value continuum and expressed by the progress bar. However, not all click-on detections result in a need to recompute the cost to treat. The thread listener 550 may account for such events by invoking a "minimal request" process. For example, as the client 503 is navigated through the EMR system 504, with the same patient selected, for each event the client 503 may use a minimal request to the HVA server 502 asking for an update to the cost value. If the value returned is the same as the current value, no further network transmissions are performed until another event is detected. If the cost values differ, then the client 503 may request an update for the rest of the patient information such as DRG, DRG description, detailed cost breakdown, etc. However, the request is only for data that have changed. In this method, the network utilization of the client is tied to comparing the currently stored cost on the client side with an updated cost on the server side. The client server engine 540 further may include a prompting module that executes to automatically generate prompts to physician providers and other health care providers based on the occurrence of certain events. The prompts may be displayed as text messages on one or more of the displays provided through the system 500, including the display 400 of FIG. 4A and the display 830 of FIG. 8C. Alternately, the prompts may be sent to an endpoint such as an account of a physician provider as, for example, a text message or an email. Prompts may provide suggestions to transition make changes to a patient's plan of care, for example.

In some embodiments, when the HVA client 508 displays comparison data (i.e., the value continuum and the corresponding progress bar) for a patient, the HVA client 508 may display data comparisons in one of several different modes. The activity surrounding the patient during a displayed admission cycle may cause the progress bar to move from green to yellow to red. The user may select the type of comparison the user wishes to see, including:

Actual and scheduled charges compared to the baseline cost to treat for the facility.

The actual and scheduled charges compared against a peer group of physicians treating similar patients. The patients may be categorized as similar based on the patients having the same diagnoses codes (e.g., DRGs, ICDs, neural network, and the like). Additionally, or alternatively, the patients may be categorized as similar based on demographic data (e.g., age, gender, location, and the like) or any other suitable grouping or shared characteristic. The peer group for a physician may be recognized by the system 500 based on other users of the system 500. The comparison costs may come from the most recent patient admissions seen by the peer group.

The actual and scheduled charges compared against physicians covering an entire region for the same diagnoses codes. The region for a physician may be recognized by the system 500 based on other users of the system 500. The comparison costs come from the most recent patient admissions seen by other users of the system 500.

The actual and scheduled charges compared against physicians of the same specialty treating for the same diagnoses codes. The same specialty group for a physician may be recognized by the system 500 based on other users of the system 500. The comparison costs come from the most recent patient admissions seen by the specialty group.

The actual and scheduled charges compared against a single physician's aggregated cost statistics for a group of patients over a period.

Figure 5E:
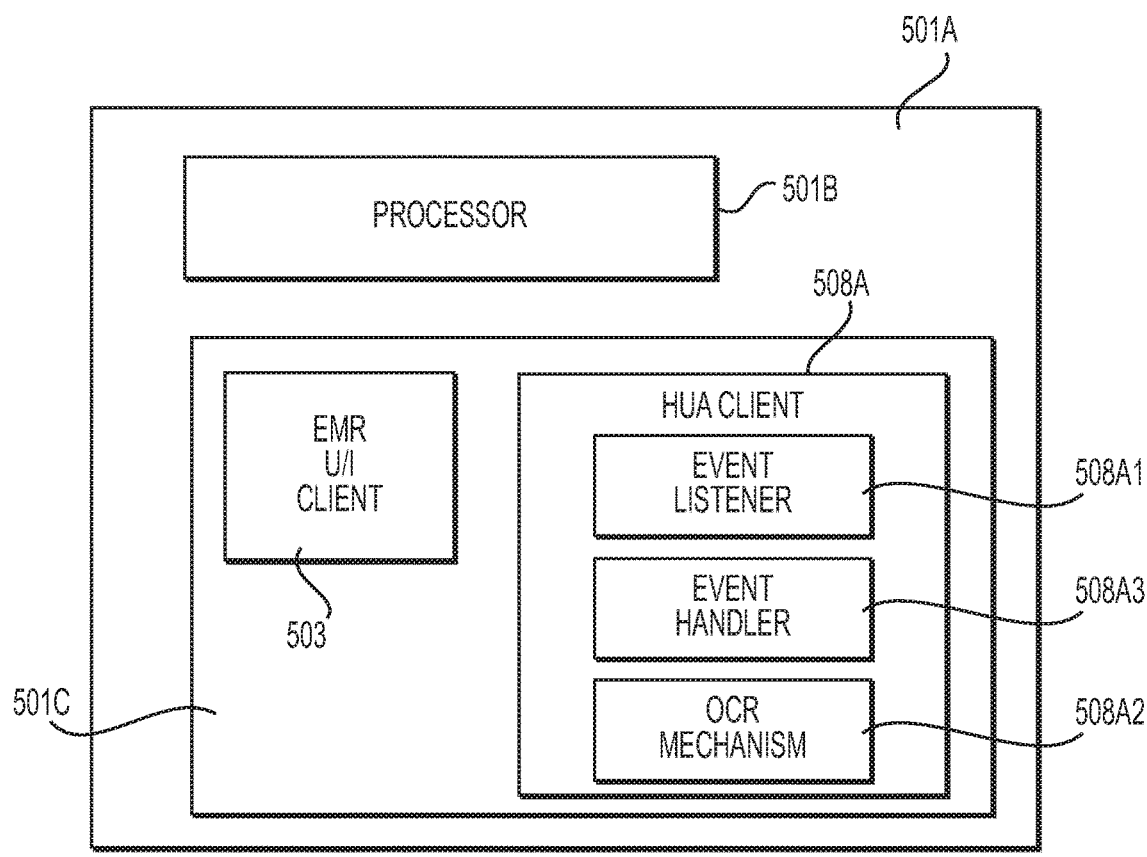
Figure 5F:
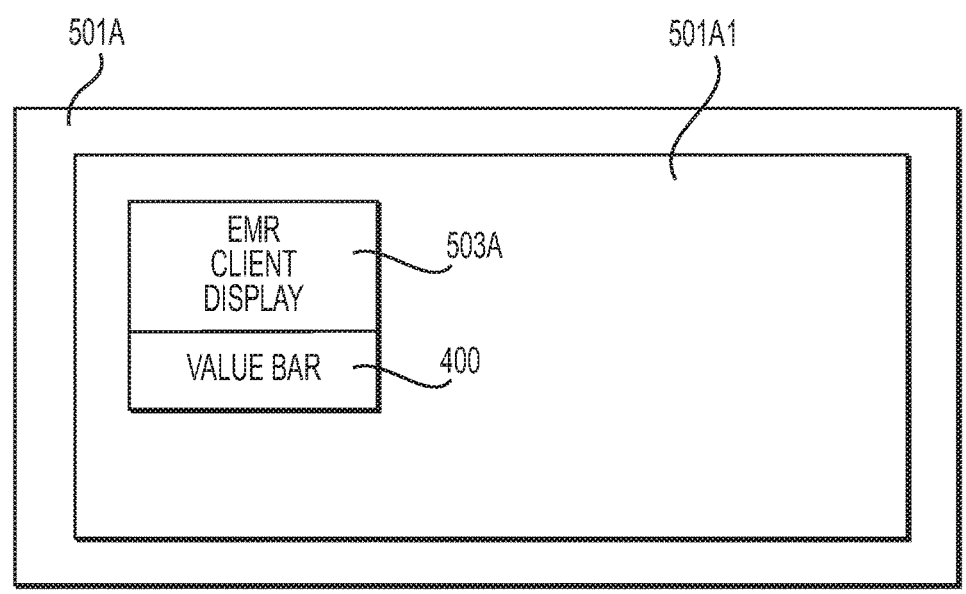

In an embodiment of the system 500 for determining and indicating value of healthcare, the physician provider device 501A may include a more fully-featured version of the HVA client 508 in that the more fully-featured version of the HVA client 508 executes processes that in other embodiments of the system 500. FIGS. 5E and 5F illustrate an embodiment of the system 500 in which HVA client 508A detects certain activities related to a visit of a patient, sends notices of the detected activity to the HVA server 502, and receives, in response to the notices, updates related to a status of a patient from the EMR system 504. In FIG. 5E, physician provider device 501A includes local processor 501B and has installed in a computer-readable storage medium 501C, EMR user interface client 503 and HVA client 508A. The EMR user interface client 503 executes as previously described with respect to FIG. 5A. The HVA client 508A includes event listener 508A1 that executes to detect activity related to execution of EMR user interface client 503. For example, the event listener 508A1 detects when the EMR user client 503 registers a new patient through creation of a patient visit ID. The event listener 508A1 also detects other activity related to a visit of a patient, such as a diagnosis, a change in plan of care for a patient, completion of a medical procedure, or addition of a medical prescription for the patient, for example. The event listener 508A1 executes in a manner similar to the thread listener 550 of FIG. 5D.

Also shown in FIG. 5E is optical character recognition (OCR) mechanism 508A2. The OCR mechanism 508A2 executes to read data from the EMR user interface client 503. Specifically, in an embodiment, the EMR user interface client 503 may execute to display information such as a visit ID on a display, and the OCR mechanism 503A2 reads the displayed visit ID, converts the image to a digital format, and uses the digitized visit ID as part of a process to generate and maintain a value bar such as the value bar 400 of FIG. 4A.

The HVA client 508A further includes event handler 508A3 that may receive information from the HVA server 502. Such information may be sent to the HVA client 508A when the HVA server 502 receives information updates from the EMR system 504. The event handler 508A3 and event listener 508A1 also may cooperate to send periodic queries to the HVA server 502 to obtain updates from the EMR system 504 about a specific patient and patient visit and to use the updates to populate the value bar. For example, after the event listener 508A1 detects a patient activity, the event handler 508A3 may periodically poll the HVA server 502 until the HVA server 502 issues an update appropriate for the detected patient activity. In an aspect, the number of polling messages may be limited to a pre-determined number. In another aspect, the event handler 508A3 may receive updates specific to a patient visit without a prior request from the event listener 508A1. The event handler 508A3 also may receive general updates applicable to all patient visits or a subset of patient visits. The HVA client 508A may execute to update the value bar based on these and other updates and information provided through the system 500.

FIG. 5F illustrates an example display screen 501A1 of the physician provider device 501A. In FIG. 5F, display screen 501A1 provides a display 503A of the EMR user interface client 503 and value bar 400 generated by the HVA server 502 in cooperation with the HVA client 508A. In an embodiment, the HVA client 508A detects the physical location of the display 503A on the display screen 501A1 and executes to place the value bar 400 in close proximity to the display 503A. For example, the value bar 400 is placed immediately above or below the display 503A. Placing the value bar 400 adjacent to the display 503A aids the physician provider in recognizing important information related to a specific patient.

In some embodiments, the system 500 may provide feedback on orders that are placed for a patient. The feedback may relate to the practices of other physicians treating patients with the same or similar diagnosis, and be based on historical information. Such historical information may be gathered over time for a particular facility, a group of facilities, a group of physicians, or any other suitable group that shares at least one characteristic. For example, if a physician orders an x-ray for a patient, the system 500 may inform the physician how frequently that x-ray order is associated with treating that diagnosis. In some embodiments, for orders that are very common with the patient's diagnosis, the system 500 might not generate an alert, but for orders that are comparatively rare (e.g., other physicians order the x-ray less than 5% of the time, or less than 20% of the time, or any other suitable threshold), the system 500 generates an alert. The alert may be displayed at the HVA client 508, and may be similar to the following: "For patients with this diagnosis, the x-ray order is only seen in 3% of the treatment plans." Similarly, the system 500 may provide feedback on orders based on best practice treatment protocols for a diagnosis. Some hospitals, facilities, and provider groups have developed best practice treatment protocols for each diagnosis. In such cases, the system 500 may provide an alert if an order is outside the predetermined protocol.

In some embodiments, the system 500 may provide information about orders commonly associated with a particular diagnosis. Such information may relate to the practices of other physicians treating patients with the same or similar diagnosis, and be based on historical information. For example, if a patient is assigned a diagnosis of pneumonia, the system 500 can inform the physician what are the most common orders prescribed for patients with a diagnosis of pneumonia. In some embodiments, the orders may be ranked by how frequently the orders are associated with treating the diagnosis (i.e., frequency of use) or by category of care (e.g., labs, radiology, etc.). As a particular example, the orders may be presented as a list that is ordered by rank and is displayed at the HVA client 508. As another example, the orders may be grouped by day or other period during a length of a visit or a length of care (e.g., most common orders for Day 1 of a hospital visit, most common orders for Day 2 of the hospital visit, etc.). In some embodiments, information about orders may be related to a total cost to treat. For example, the system 500 may inform the physician which orders have been historically associated with patients whose total cost to treat was less than a baseline cost to treat, as a way of indicating that such orders are associated with good outcomes. In some embodiments, the physician may select orders directly from the displayed list.

In some embodiments, the HVA server 502 may send alerts or prompts (or links to alerts or prompts) to be displayed with the value continuum (e.g., the display 830 of FIG. 8C) when a patient's treatment plan changes. As an example, a patient may initially be assigned a length of visit of three days; however, if complications arise, the length of stay may be extended, and additional procedures may be normal for such an extension. The HVA server 502 may send an alert or prompt to be shown on the display 830 suggesting possible additional procedures for the physician to consider ordering for the patient.

In some embodiments, when a patient is discharged, a communication may be sent to the HVA server 502 so that an end of a visit may be recorded for the patient. Once this event occurs, further communications from the EMR system 504 may not be needed for this patient. The system 500 may maintain a persistent HVA value analysis for a discharged patient (e.g., at a database in the HVA server 502).

The progress bar is displayed in the HVA client 508 based on the expected reimbursement or expected cost to the hospital or facility to treat the patient; this cost is based on the diagnosis for the patient. It is common for the DRG to change throughout the facility visit period. In such cases, the progress bar displayed in the HVA client 508 may be updated to reflect the change whenever a new DRG code is received for a patient. Similarly, the baseline cost to treat may be modified at one or more points during a patient visit based on how the patient progresses, the outcome of one or more procedures, and the like.

In some cases, a working DRG code and illness severity may not be available when a patient is admitted to the hospital or facility. In fact, it may be many hours or even days later before even a working DRG code is known. In some embodiments, the HVA client 508 may indicate that no DRG is currently available for this patient. In some embodiments, the system 500 may use a generic baseline DRG or a baseline diagnosis that is discerned from initial evaluation of patient symptoms.

Because some payment reform models are trending toward a single lump sum payment to a facility that includes health care provider fees, in some embodiments, the baseline cost to treat may include both facility costs and health care provider (e.g., physician) fees. Additionally, from that single payment, physicians and other health care providers may need to negotiate their fees with the facility. The system 500 may facilitate a "share in savings" model where the physician fees are based on the value (cost versus reimbursement) the physician provided to the patient.

Although FIG. 5A illustrates one example of a system 500 for determining and indicating value of health care, various changes may be made to FIG. 5A. For example, various components in FIG. 5A may be combined, further subdivided, rearranged, or omitted and additional components may be added according to particular needs.

Figure 6:
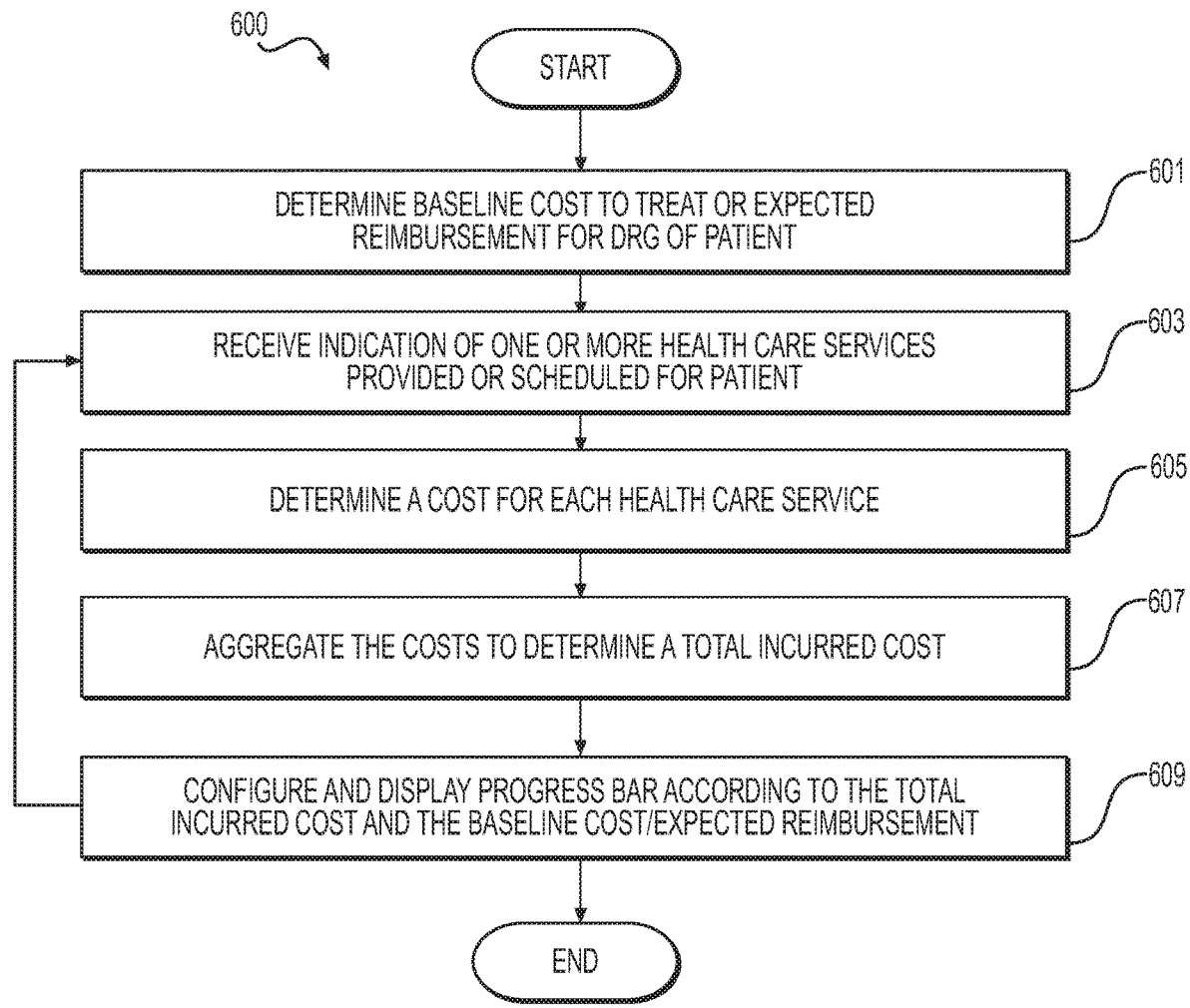
FIG. 6 illustrates an example operation of the systems of FIGS. 5A-5F.

FIG. 6 illustrates an example method 600 for determining and indicating value of health care according to this disclosure. For ease of explanation, the method 600 is described as being performed using the system 500 of FIGS. 5A-5D. However, the method 600 may be used with any suitable device or system.

At block 601, the system 500 determines an expected cost to treat, an expected reimbursement, or both, for a DRG associated with a patient. This may include, for example, the HVA server 502 calculating the expected cost to treat based on a baseline cost of treatment for all patients having the same diagnosis that are treated by a predetermined group of physicians (e.g., the physicians affiliated with the health care facility) over a predetermined historical period (e.g., the two previous years) or at a predetermined group of health care facilities over a predetermined historical time period. Additionally, or alternatively, block 601 may include the HVA server 502 calculating the baseline cost to treat based on a designed plan of care for the DRG.

At block 603, the system 500 receives an indication of one or more health care services provided or scheduled for the patient. Block 603 may include, for example, a health care provider (e.g., a physician) entering one or more orders into the CPOE 504A and then the HVA server 502 receiving the order or an indication of the order from the EMR system 504.

At block 605, the system 500 determines a cost for each of the health care services. Block 605 may include, for example, the HVA server 502 obtaining the cost(s) from the facility charge master 506A or calculating the cost(s) based on information from the facility charge master 506A.

At block 607, the system 500 aggregates the costs for the health care services to determine a total aggregated cost. Block 607 may include, for example, the HVA server 502 adding each of the individual costs together.

At block 609, the system 500 configures an indicator to indicate the total aggregated cost relative to the expected cost to treat or the expected reimbursement, and then displays the indicator to a user. Block 609 may include, for example, the HVA server 502 configuring a progress bar, such as the progress bars 304, 404, and 424. Once the progress bar is configured for display, a client application, such as the HVA client 508 may display the progress bar. In an aspect of block 609, the HVA client 508 may detect where on a screen of the device (e.g., the physician provider device 501A) the display of the HVA client 503 is presented, and may adjust the position of the value bar and progress bar to be adjacent to the display of the EMR user interface 503.

Block 603-609 may be repeated as the health care provider enters new orders or new costs are aggregated. All operations described in method 600 may be performed in real-time in to provide a real-time display to a user as patient orders are entered and costs are aggregated.

Although FIG. 6 illustrates one example of a method 600 for determining and indicating value of health care, various changes may be made to FIG. 6. For example, while shown as a series of operations, various block shown in FIG. 6 may overlap, occur in parallel, occur in a different order, or occur multiple times. Moreover, the operations of some blocks may be combined or removed and additional operations may be added according to particular needs.

Figure 7A:
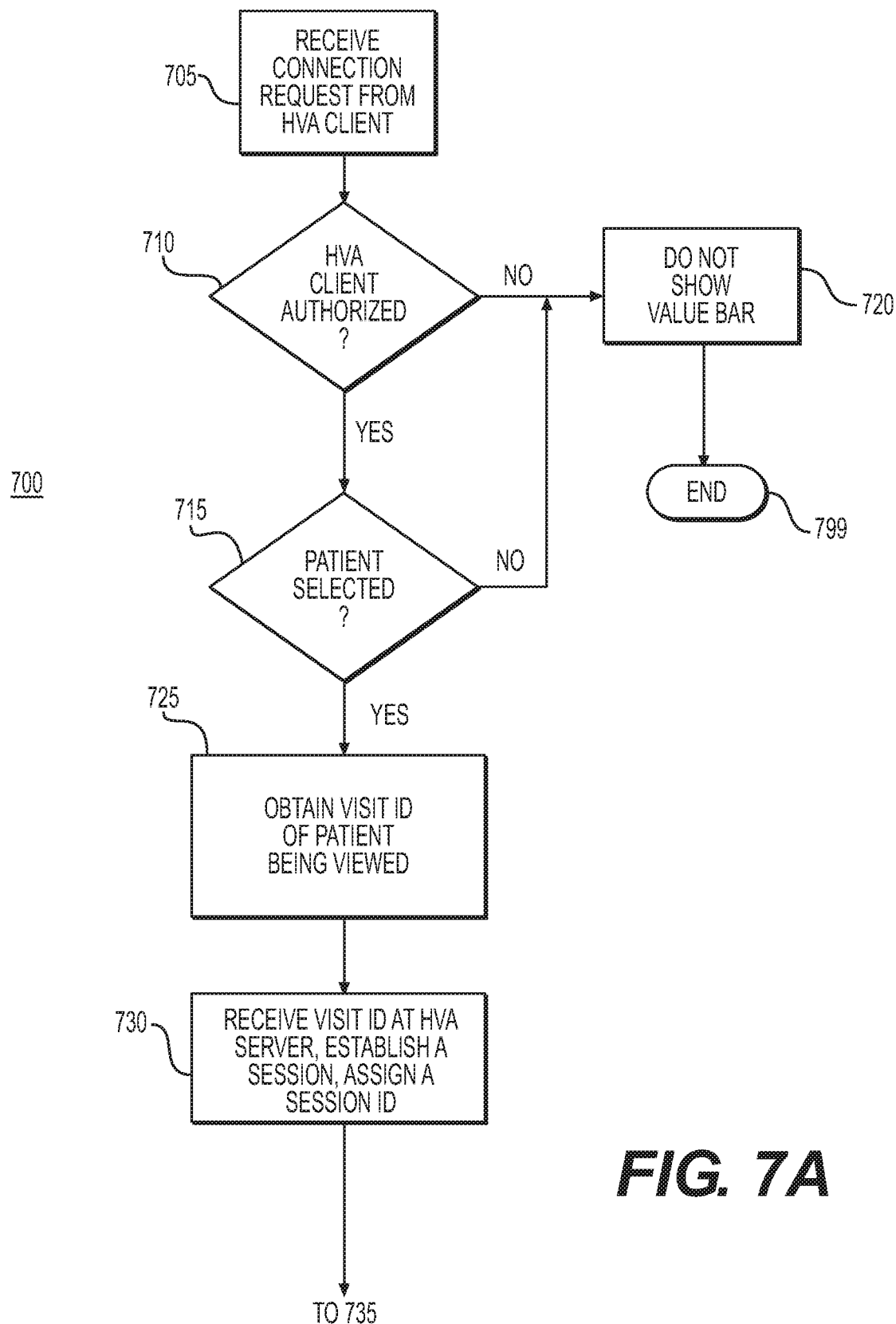
FIGS. 7A-7D illustrate another example operation of the systems of FIGS. 5A-5F.
Figure 7B:
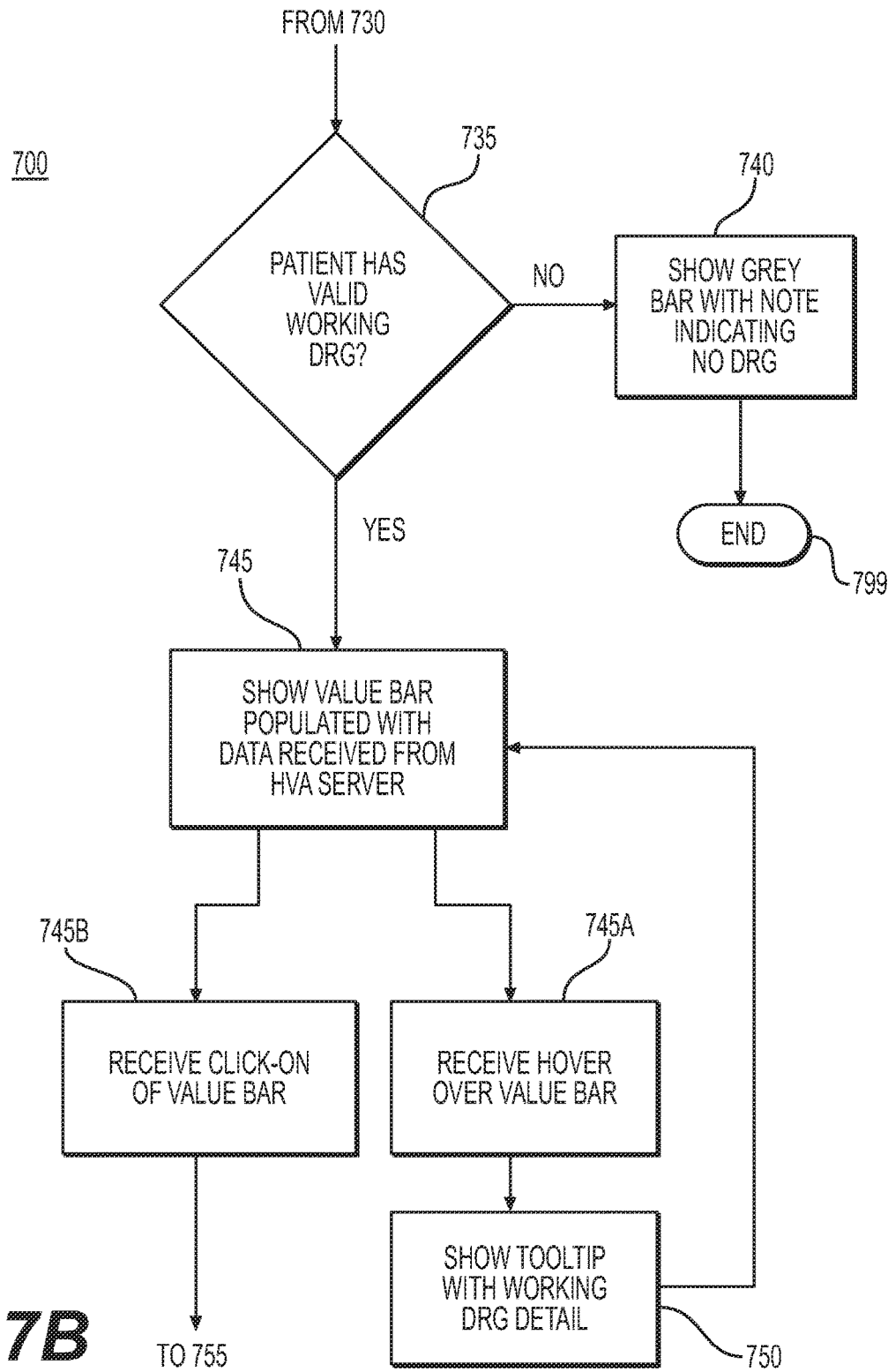
Figure 7C:
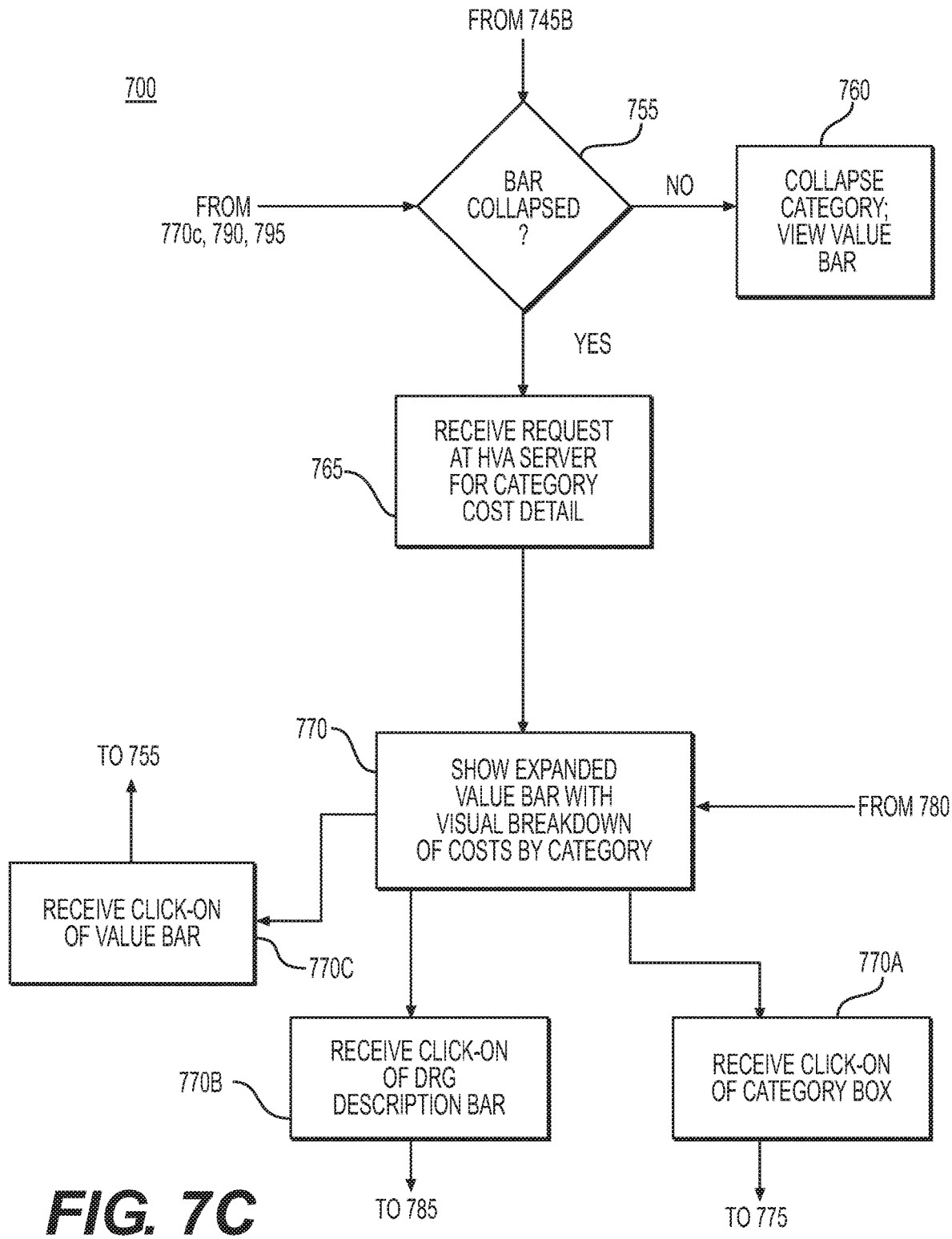
Figure 7D:
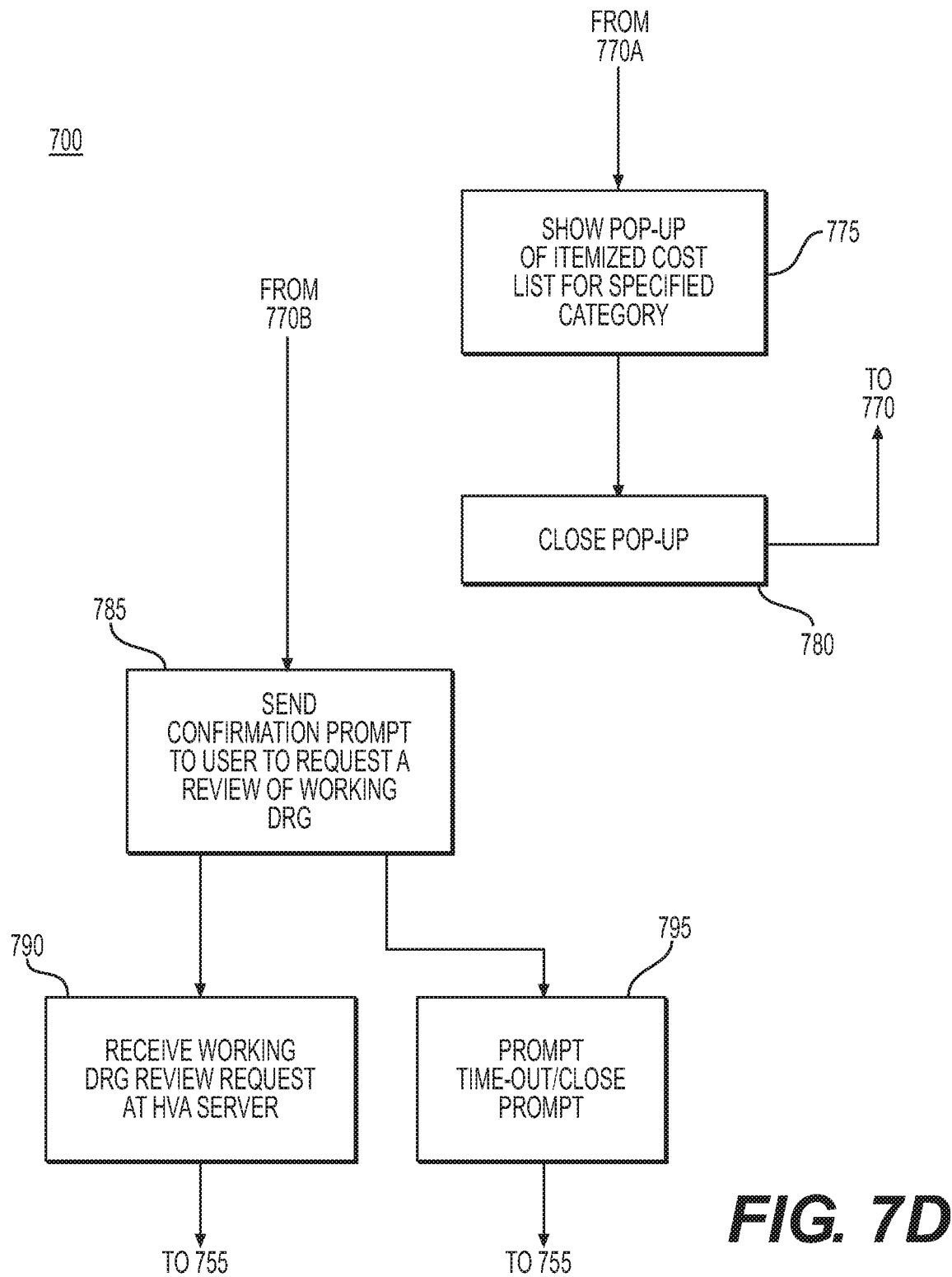

FIGS. 7A-7D illustrate still another example operation of components of the system 500 of FIGS. 5A-5D, most notably, interaction between the HVA client 508 and the HVA server 502 to display the value continuum and corresponding progress bar. The illustrated operation is based on a scenario involving operation of the system 500 in which physician provider device 501A accesses EMR user interface client 503 to view electronic medical records for an existing patient, the records stored in the EMR system 504, as part of a hospital admission process. In FIG. 7A, operation 700 begins in block 705, when the HVA client 508 (through, for example, the thread listener 550) detects an event or activity that may warrant generation and display (or update and display) of a value continuum and corresponding progress bar; in this example, the activity is log on to the EMR system 504 by the physician provider 501A and the HVA server 502 receives an address of the HVA client 508, and the HVA client 508 receives a Session ID associated with the log on. In block 710, the HVA server 502 determines if the address is appropriate; for example, the HVA server 502 may determine if the address is a "recognized" or "approved" address—that is, an address appropriate for the EMR system 504. In block 710, if the address is "not appropriate," the operation 700 moves to block 720 and the HVA client 508 does not send a request 507 to the HVA server 502, and the HVA server 502 does not present data necessary for the HVA client 508 to display the value continuum and the corresponding progress bar. Following block 720, the operation 700 moves to block 799 and ends. In block 710, if the address is appropriate, the operation 700 moves to block 715, and the HVA server 502 determines if the physician provider activity (i.e., the example log in to the EMR system 504) identifies a patient by Visit ID in the EMR system 504. Typically, a new or first-time patient may be entered into the EMR system 504 as a new patient as part of the log in that precedes the operation 700. This initial entry may include the patient being assigned a Visit ID. In an embodiment, the Visit ID may be entered electronically as part of the new patient admittance order. In another embodiment, the Visit ID may be manually entered on the admittance order. In yet another embodiment, through a process of screen capture and optical character recognition, a component of the system 500 may access the display of the EMR user interface client 503, perform a screen capture, detect the Visit ID of the patient, and perform an OCR process to convert the displayed Visit ID to a digital format for use by the HVA server 502. In some embodiments, the Visit ID assigned upon admittance is synonymous with the Session ID. In other embodiments, the Visit ID and Session ID are related in the HVA server 502 and EMR server 504. If a patient is not selected from patients in the EMR system 504 (or a new patient identified), the operation 700 returns to block 720, and ultimately ends, block 799. If in block 715, a patient from the EMR system 504 is selected, the operation 700 moves to block 725.

In block 725, the HVA client 508 obtains the Visit ID (or, simply, a visit) of the selected patient, and in block 730 the HVA server 502 receives the Visit ID for use in further processes under operation 700. For example, in block 735, the HVA server 502 determines, based on the visit, if the selected patient has a valid working DRG. If the selected patient does not have a valid working DRG, the operation 700 moves to block 740 and the HVA server 502 responds to the request 507 to show at the HVA client 508 display, a grey bar with a note that the selected patient does not have a working DRG (the working DRG may be created by execution of other operations such as the physician provider device 501A accessing the CPOE module 504A to enter orders and the CDI specialist device 501B entering appropriate medical codes). The operation 700 then moves to block 799 and ends. In block 735, if the selected patient does have a valid working DRG, the operation 700 moves to block 745, and the HVA server 502 provides information to the HVA client 508 to cause display of a value continuum and a corresponding progress bar populated with data extracted by the HVA server 502 from the EMR system 504. In an aspect of block 745, the value continuum and corresponding progress bar may be placed in an optimum position of the display screen of the devices 501A or 501B. For example, programming in the HVA client 508 may detect the physical location of the display of the EMR user interface client 503 and position the value continuum below or above the display of the EMR user interface client 503. Following block 745, the operation 700 proceeds to block 745A or 745B, depending on a request 507 from the HVA client 508. In block 745A, the HVA client 508 receives an activity signal generated by hovering of a cursor or other pointing device over the progress bar displayed through the HVA client 508, and sends a minimal request 507 to the HVA server 502. In response, the HVA server 502 determines if information related to the patient and the patient's treatment plans is available and, if so, provides information and instructions (block 750) that cause the HVA client 508 to display a pop-up display (see FIG. 8B) with working DRG details, on the display of the HVA client 508. The pop-up display of block 750 persists as long as the cursor hovers over the progress bar. Once the hovering ends, the operation 700 returns to block 745, and the HVA server 502 causes the pop-up display to end. If, following block 745, the HVA server 502 receives a request 507 based on detection by the HVA client 508 of a click-on of the progress bar, the operation 700 moves to block 755, and the HVA server 502 receives request 507 from the HVA client 508 indicating if the progress bar is, or is not, collapsed. If in block 755, the HVA server 502 receives a request 507 that the progress bar is not collapsed, the HVA server 502 provides information and instructions that cause the category to collapse and the progress bar to be displayed. If in block 755, the HVA server 502 receives a request that the progress bar is collapsed, the operation 700 moves to block 765, and the HVA server 502 receives a request 507 to display category cost detail (see, for example, the category cost dials of FIG. 8A). Note that in blocks 745-765, the HVA client 508 may send one request 507 embodying all the data requests of the individual requests of blocks 745-765. In response to the request 507 received at block 765, the operation 700 moves to block 770, and the HVA server 502 provides information and instructions to display an expanded progress bar with a visual breakdown of costs by category (see the example display 800 of FIGS. 8A and 8B). The categories may include one or more of Radiology, Pharma, Hospital Room, Procedures, Therapy, Lab, and Other, for example.

When the expanded progress bar (FIGS. 8A and 8B) is displayed through the HVA client 508, the HVA server 502 may receive one of three requests. In block 770A, the HVA server 502 may receive a request based on detection of a click-on of a category box; in block 770B, a click-on of a DRG description bar; and in block 770C, a click-on of the progress bar. Following block 770C, the operation 700 returns to block 755. Following block 770A, the operation 700 moves to block 775, and the HVA server 502 provides information and instructions that cause the HVA client 508 to display a pop-up of the itemized cost list for the specified category. Following display of the pop-up in block 775, the HVA server 502 may receive, block 780, a close pop-up request and may provide information and instructions to the HVA client 508 to cause the pop-up to close. Alternately, a user may execute a close instruction that is part of the pop-up, and is represented, for example, by an "X" appearing on the pop-up. In either event, following closure of the pop-up, the operation 700 returns to block 770. Following block 770B, the operation 700 moves to block 785, and the HVA server 502 sends information and instructions to display at the HVA client 508, a confirmation prompt to prompt a user of the HVA client 508 to confirm a request for a review of the working DRG. In response to the prompt, the HVA server 502 may receive, block 790, a request 507 for a working DRG review. Otherwise, after a set time, the HVA server 502 causes the prompt to close, block 795. Following either block 790 or 795, the operation 700 returns to block 755.

FIGS. 8A-8C illustrate example displays for determining and indicating value of health care that may be generated by the system of FIGS. 5A-5D. The displays of FIGS. 8A-8C may be presented on a screen of physician provider device 501A. In an embodiment, the HVA client 508 may execute to present the displays near the EMR user interface client display. FIG. 8A illustrates HVA display 800, which is seen to include value continuum 801, which in turn includes progress bar 804. The value continuum 801 also includes a breakout of value continuum categories (for example, Pharma, with cost progress represented by dials 806). The dials 806 show the same regional green, yellow, and red scales as the progress bar 804 for each component of the patient's treatment plan (the designed plan of care). Note that the value continuum and progress bar are shown expanded—the individual categories (Radiology, Lab, Procedures, Therapy, Pharma, Room, Other) are broken out, as opposed to what would be shown in a collapsed progress bar format such as that of FIG. 4A. The display 800 also shows current length of stay 805 for the patient. Finally, assuming the display 800 is provided to a physician provider, the display 800 may include a list 810 all patients of the physician provider, and the physician provider may click on any of the patients to determine the cost to date for a visit of the patient. (Note that the thread listener 550 may detect such a click-on as an activity that may trigger a need to recompute the patient's value continuum and that would trigger a request to stop display of the value continuum for the previously selected patient.).

FIG. 8B shows display 800 with a drill down to show a cost comparison and related data 820 for a prescription order placed by the physician provider for a currently selected patient. The cost comparison and related data 820 includes charge code, description, cost, and a comparison to the number (percentage) of visits with the same charge code.

FIG. 8C illustrates a value portal and alert system display 830. The display 830 may include, for each patient visit (referenced by Visit ID 833), DRG status 831, indicating if a working DRG exists and is tracking, as well as a DRG reference 832. The display 830 further includes a cost alert 834 showing cost progress to date as a percentage of expected cost to treat for the reference DRG. The display 830 still further includes hospital room assignment data, procedure data and admission data 836. Finally, the display 830 includes physician DRG reviews ordered 838. Note that some of the data presented in the display 830 includes data useable by the HVA client 508 during execution of operation 700 (FIGS. 7A-7D) to determine whether to send a request to the HVA server 502. For example, if a DRG does not exist for a specific Visit ID 833, the HVA client 508 does not send a request to the HVA server 502.

Figure 9A:
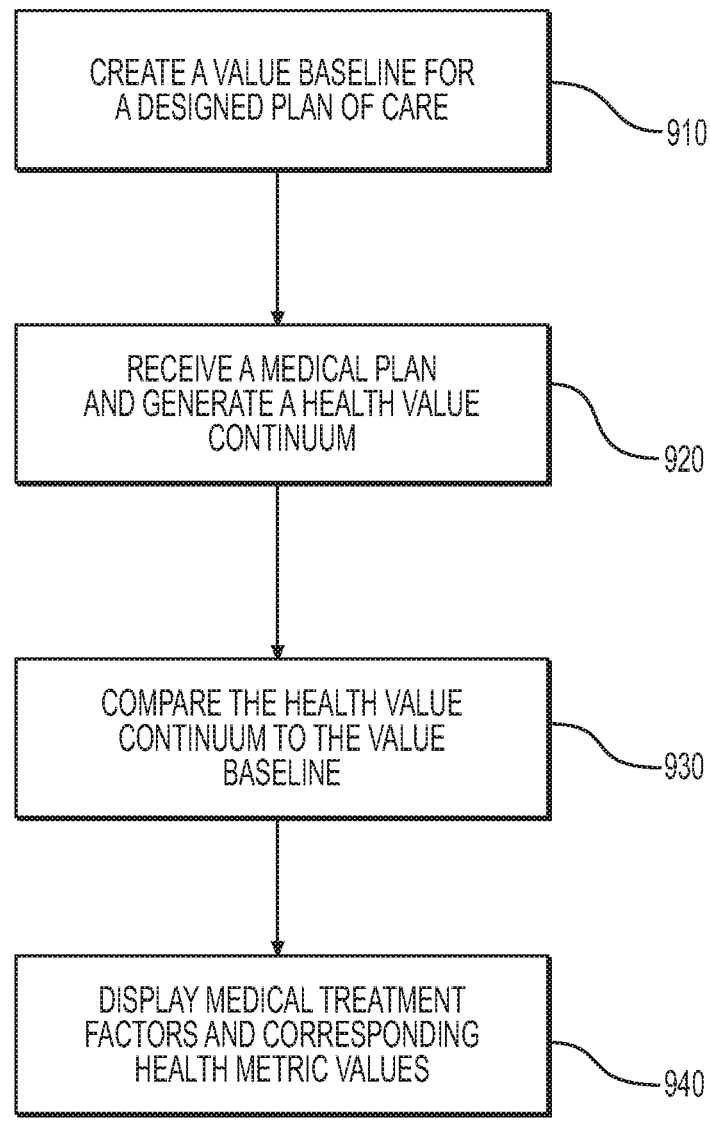
FIGS. 9A-9D illustrate another example operation of the systems of FIGS. 5A-5F.

FIGS. 9A-9D illustrate yet another example operation of the system of FIGS. 5A-5D. In FIG. 9A, operation 900 begins in block 910 with the HVA server 502 creating a value baseline for a designated plan of care. In block 920, the HVA server 502 receives a medical plan and generates a health value continuum. In block 930, the HVA server 502 compares the health value continuum to the value baseline. Finally, in block 940, the HVA server 502 displays medical treatment factors and corresponding to the health value metrics.

Figure 9B:
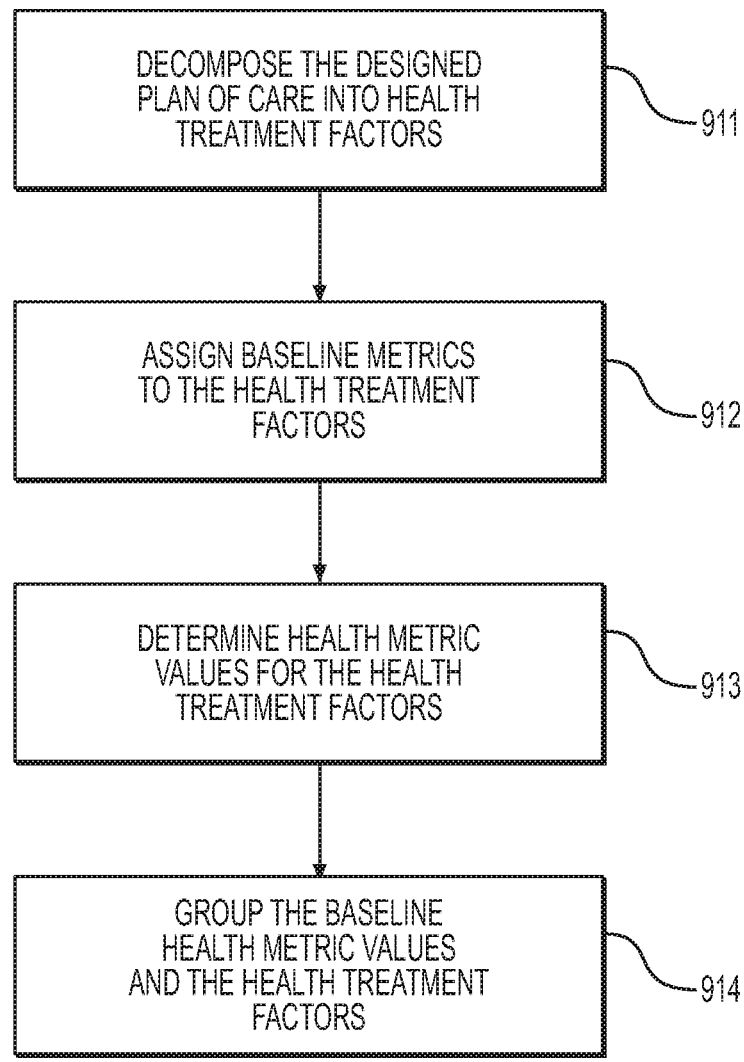

FIG. 9B illustrates the operation 910 in detail. In block 911, the HVA server 502 operates to decompose the designed plan of care into individual health treatment factors. In block 912, the HVA server 502 operates to assign baseline metrics to the health treatment factors. In block 913, the HVA server 502 operates to determine health metric values for the health treatment factors. Finally, in block 914, the HVA server 502 operates to group the baseline health metric values and the health treatment factors to create the value baseline for the designated plan of care.

Figure 9C:
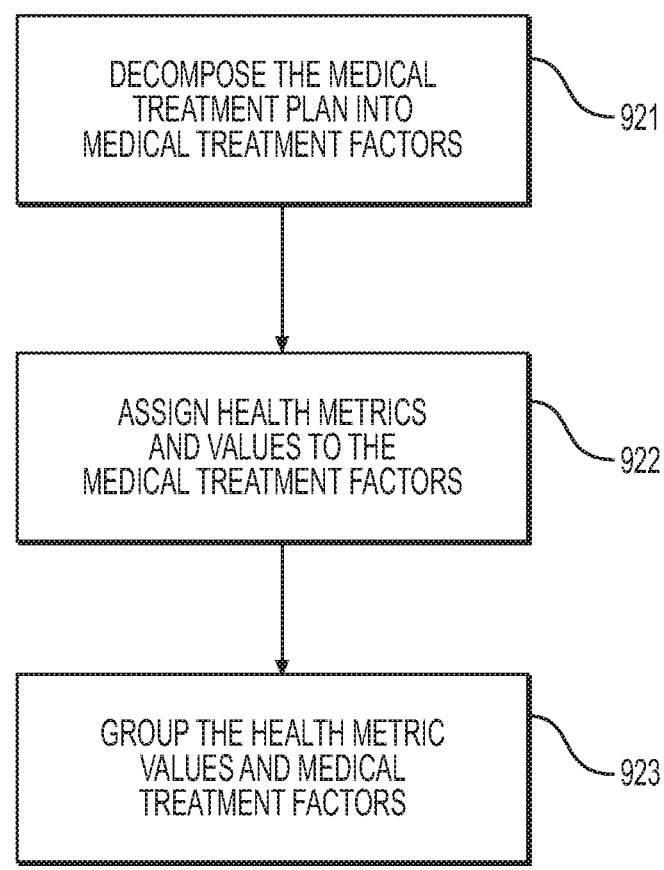

FIG. 9C illustrates operation 920 in detail. In block 921, the HVA server 502 operates to decompose the medical treatment plan into medical treatment factors. In block 922, the HVA server 502 operates to assign health metrics and corresponding values to the medical treatment factors. Finally, in block 923, the HVA server 502 operates to group the health metric values and medical treatment factors to generate the health value continuum.

Figure 9D:
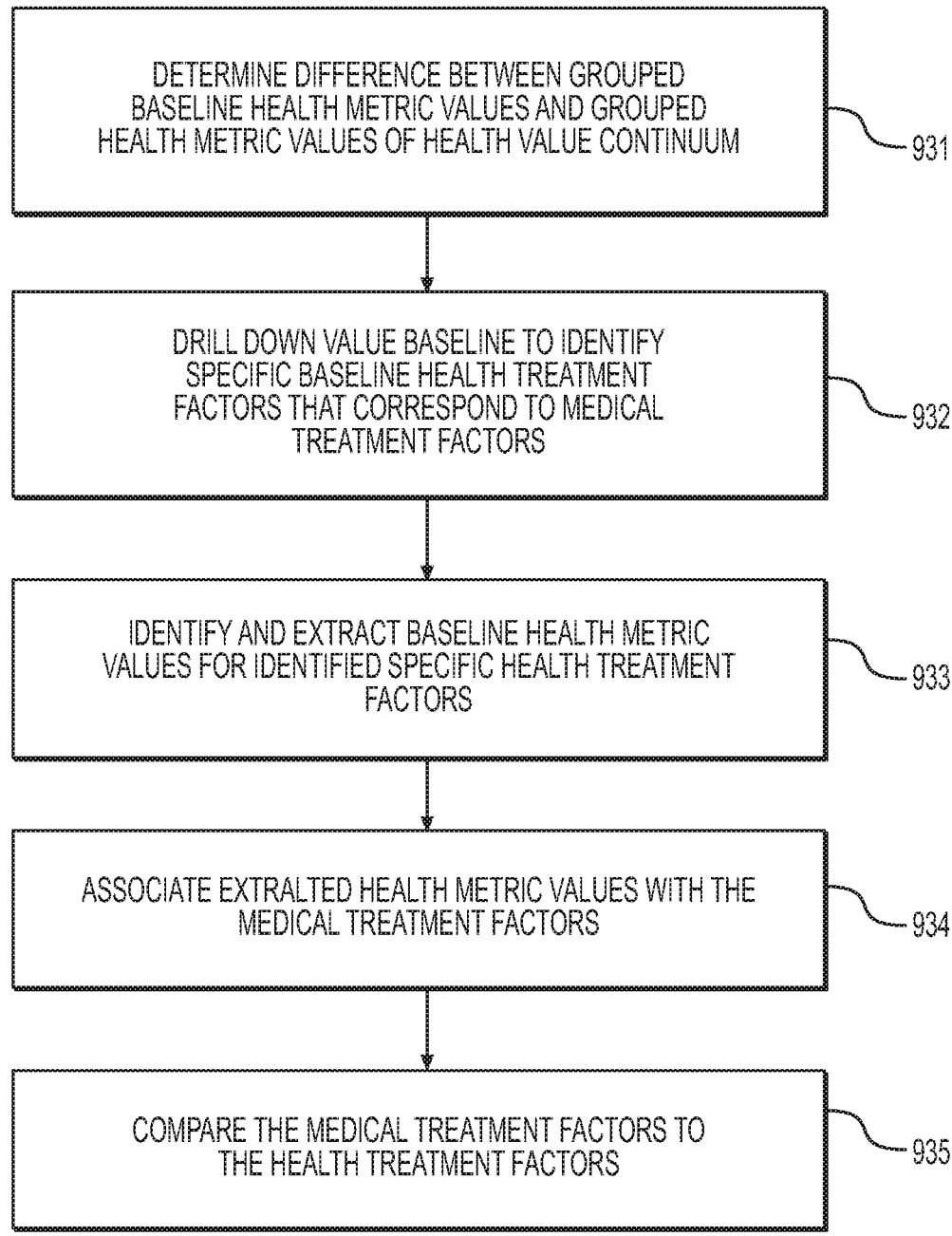

FIG. 9D illustrates the operation 930 in more detail. In block 931, the HVA server 502 operates to determine a difference between the grouped baseline health metric values and the grouped health metric values of the health value continuum. In block 932, the HVA server 502 operates to drill down the value baseline to identify specific baseline health treatment factors that correspond to medical treatment factors. In block 933, the HVA server 502 operates to identify and extract baseline health metric values for the identified specific health treatment factors. In block 934, the HVA server 502 operates to associate the extracted health metric values with the medical treatment factors. Finally, in block 935, the HVA server 502 operates to compare the medical treatment factors to the health treatment factors.

FIGS. 10A-10C illustrate alternate embodiments of a system for determining and indicating value of health care. In FIG. 10A, system 1000 includes EMR system 1004, which is seen to include health valuation analytics (HVA) server 1002. The HVA server 1002 may be accessed by HVA client 1008. The EMR system 1004 may be accessed by EMR user interface client 1027. The HVA client 1008 and EMR user interface client 1027 may be separate applications installed on and executed by physician provider device 1029. The EMR system 1004 may be accessed by CDI specialist device 1021 (for code entries, for example) and operating room scheduler 1023. The EMR system 1004 may access an external CPOE client 1023. Finally, the EMR system 1004 may access various data stores including facility charge master 1011, historical visit by baseline DRG cost 1013, baseline cost to treat DRG 1015, and expected patient cost 1017. However, the data stores 1013, 1015, and 1017 may be combined, and are part of the EMR system 1004.

Aspects of operation of the system 1000 differ from those of the system 500 of FIGS. 5A-5D because of incorporation of the HVA server 1002 into the EMR system 1004. In particular, communications between a separate HVA server 1002 and the EMR system 1004 no longer exist since the HVA server 1002 is integrated into the EMR system 1002. With this integrated architecture, the various cost analytics and value continuum analytics are executed, however, using a minimal request and event or activity listening protocol that is similar to that employed in the system 500 of FIGS. 5A-5D. For example, a physician provider, operating the device 1029, may add an order to a patient's treatment plan using the EMR user interface client 1027 (and the CPOE 1023), and the HVA server 1002 may determine that such activity warrants possible recomputation of the value continuum and progress bar. Thus, similar events occurring in the system 500 and in the system 1000 may be handled similarly.

FIG. 10B illustrates system 1100 for determining and indicating value of health care, in which EMR system 1110 is seen to include EMR server 1120 and EMR user interface and HVA client 1130. EMR system 1110 is coupled to HVA server 1140 and user device 1140. The HVA server 1140 connects to HVA data store 1141. The EMR server 1120 includes processor 1122 and records store 1124, which houses the patient electronic medical records. Note that in FIG. 10B, the EMR system 1110 may be within a firewall and the other illustrated components may be outside a firewall; alternately, all components of the system 1100 may be inside a firewall or other combinations of components may be inside or outside the firewall.

Aspects of operation of the system 1100 may differ from operation of the system 500 of FIGS. 5A-5D in some respects. For example, when a physician provider operates user device 1150 to enter an order, the HVA server 1140 client 1130 may determine if the order corresponds to an event or activity that warrant possible recomputation of the value continuum and progress bar established for a current visit of the patient receiving the order. If recomputation may be necessary, the EMR system 1110 sends a minimal request to the HVA server 1140. The HVA server 1140 may access data from the EMR server 1120 and execute instructions to recompute the value continuum and progress bar data. The HVA server 1140 then sends a response to the HVA server 1120, and the EMR/HVA client 1130 presents the updated value continuum and progress bar for viewing by the physician provider operating the user device 1150.

FIG. 10C illustrates system 1200 for determining and indicating value of health care, in which EMR system 1210 is seen to include integrated EMR/HVA server 1120, which accesses records store 1230. Records store 1230 includes patient electronic medical records and HVA data. The EMR system 1210 may be behind a firewall. Alternately, all components of the illustrated system 1200 may be inside a firewall. A CDI specialist may operate device 1260 to access the EMR system 1210. A physician provider may operate device 1250 to access the EMR system 1210. The device 1250 may have installed separate or integrated EMR/HVA clients—in FIG. 10C the applications are integrated as EMR/HVA client 1240. The integrated HVA/EMR server 1220 executes to perform operations similar to those of the client applications of FIGS. 5A-5D, 10A and 10B.

Any of the systems of FIGS. 5A-5D and 10A-10C may, in addition to the above-disclosed features, invoke additional features to further improve bandwidth utilization and reduce network load, particularly during peak periods of operation. For example, the HVA client 508 and HVA server 502 (and the EMR system 504) of FIG. 5A may invoke quality of service protocols that prioritize request and response movement in the system 500. As an example, the first activity the thread listener 550 may detect may be an initial log in by a physician provider to admit a patient to the hospital (presumably, the physician provider has established a Visit ID and provided a diagnosis and one or more orders (a medical treatment plan) for the patient). As noted above, such activity may cause the HVA server 502 to generate a value continuum for the patient/Visit ID. Such a request may, in the system 500, be accorded a higher priority than other requests from the same or other HVA clients, and the request, therefore, is moved ahead in a queue above pending update requests. In another example, the HVA server 502 may determine that a new order, or a navigation event, is a minor event, and may delay submission of the corresponding request based on monitored processor utilization. In either situation, however, request handling and response occur quickly, and, as perceived by the providing physician, occur in "real time."

Figure 11A:
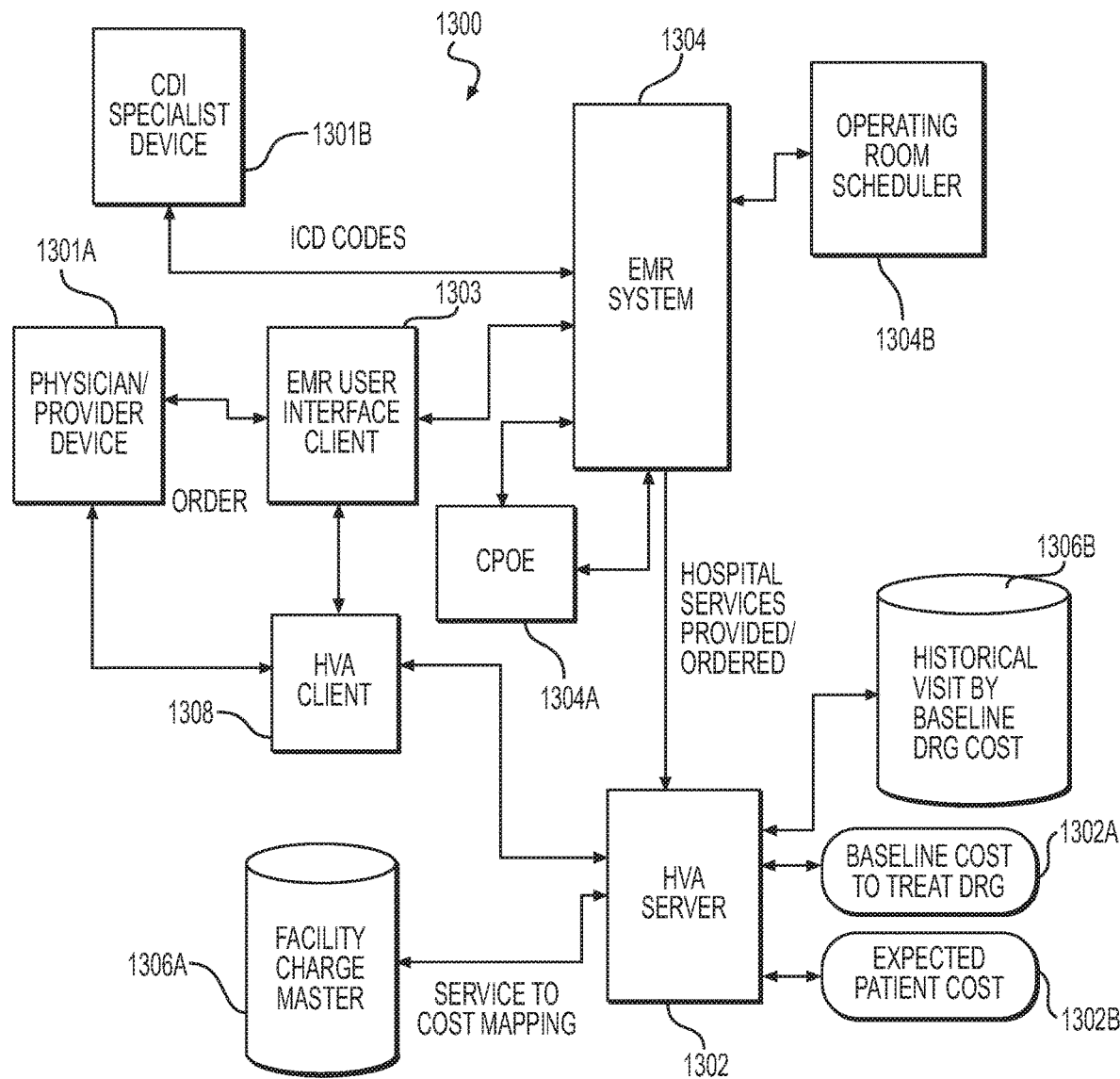
FIGS. 11A-11D illustrate yet another example system for determining and indicating value of health care.

FIG. 11A illustrates another example system 1300 for determining and indicating value of health care. One or more components of the system 1300 may represent, or be represented by, one or more components of the system 100 of FIG. 1. The system 1300 includes Health Value Analytics (HVA) server 1302, EMR system 1304, facility charge master data source 1306, and one or more HVA clients 1308. The EMR system 1304 includes a server and records store (not shown). The system 1300 further includes computerized physician order entry (CPOE) module 1304A, operating room scheduler 1304B, EMR user interface client 1303, and data source 1306B (historical visit by average DRG cost). The HVA server 1302 produces baseline cost to treat DRG 1302A and expected patient cost 1302B. The EMR system 1304 may be accessed and used by health care providers such as a physician provider at physician provider device 1301A and hospital staff, such as a CDI specialist, at CDI device 1301B. In an embodiment, some components of system 1300 may be software programs instantiated on system 1300 hardware devices. For example, COPE module 1304A may be a software module resident on a component of EMR system 1304. In this example, a physician may access EMR user interface client 1303 and invoke CPOE module 1304A to enter patient orders. In an embodiment, the components of the system 1300 may be behind a firewall such that communications between and among the components are simplified, and communications security is enhanced. In an aspect, the EMR system 1304, devices 1301A and 1301B, CPOE 1304A and operating room scheduler 1304B, and EMR user interface client 1303 may be components of a legacy hospital system while the HVA server 1302 and HVA client 1308, and associated data stores 1302A, B, and 1306A, B, may be added to, integrated with, or simply in communication with the legacy hospital system.

The HVA server 1302 may be a back-end server (similar to the server 112 of FIG. 1) that connects (via a network connection) to the EMR system 1304 for the hospital system or group where the system 1300 is installed. The system 1300 may work with any EMR system 1304. In an embodiment, the HVA server 1302 receives order information, patient information, and the like from the EMR system 1304 by executing commands to retrieve the information from the EMR system 1304 database. In another embodiment, the HVA server 1302 receives order information, patient information, and the like from the EMR system 1304 by, for example, an HL7 interface (not shown) to the EMR system 1304.

The facility charge master data source 1306A may be a database, data table, or other data source that includes charge information for a hospital or other facility. The HVA server 1302 may store or access the charge information from the facility charge master data source 1306A, and use the information from the data source 1306 to convert orders received from the EMR system 1304 to one or more costs. In an embodiment, the facility charge master data source 1306A may be received by the HVA server 1302 as a file (e.g., via email). The file then may be loaded into the HVA server 1302. Alternately, the HVA server 1302 may connect directly to the hospital or facility accounting system to retrieve these charges. Ultimately, it is hospital or facility costs that are used in the system 1300; these may be determined simply by multiplying a cost-to-charge ratio factor by the charges or have a table or method of calculating costs from the orders.

The EMR user interface client 1303 may be implemented as software or hardware. In an aspect, the EMR user interface client 1303 is accessed by physician provider device 1301A to connect to the EMR system 1304 and, by way of HVA client 1308, the HVA server 1302.

Each HVA client 1308 may be accessed on a client device or other end-user device with a display (such as one of the end user devices 104-110 of FIG. 1) and provides functionality for users of the system 1300 to view on the health care value continuum. Each HVA client 1308 may exchange information with the HVA server 1302 over a secure network link via one or more custom APIs.

Each HVA client 1308 may be installed on a client device as a stand-alone application or as a plug-in. Alternately, each HVA client 1308 may reside on a central device (e.g., the HVA server 1302) and be accessed by a client device via a portal such as a web browser.

Figure 11B:
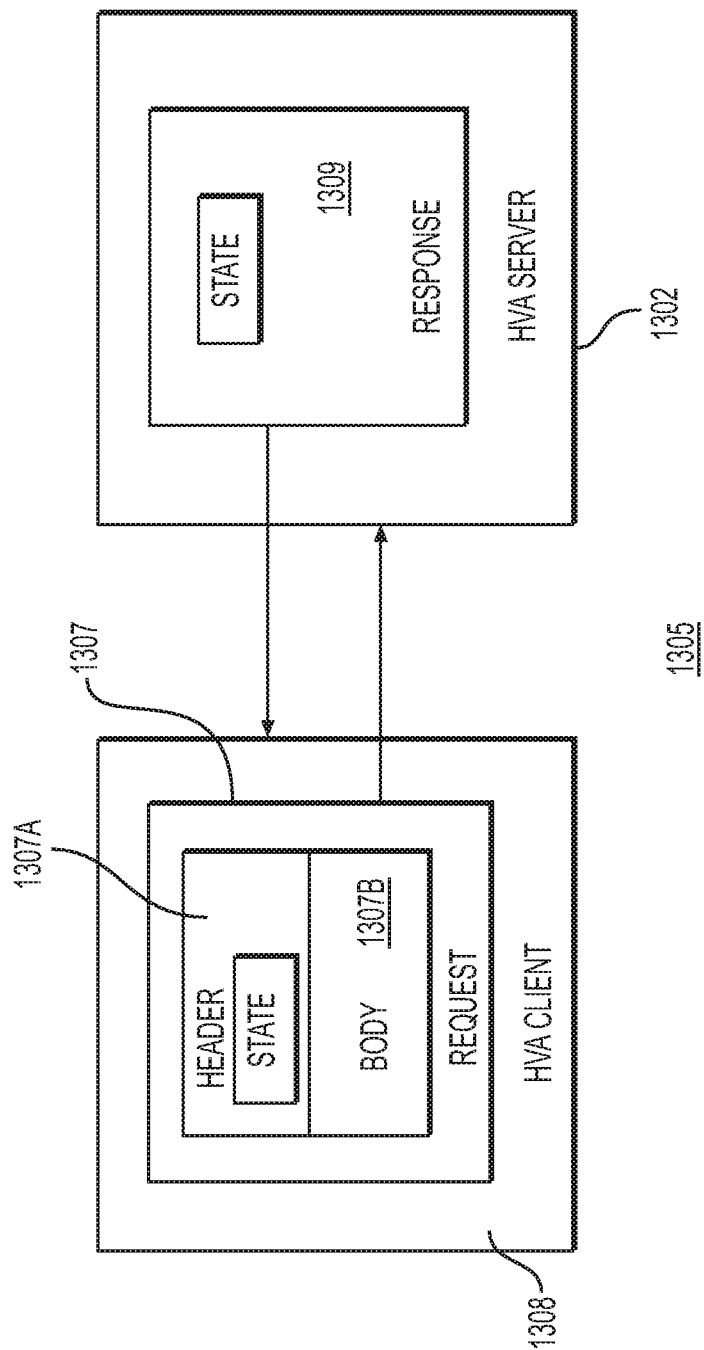

In an embodiment, the HVA client 1108 and the HVA server 1102 communicate using a stateless transfer architecture and protocol, a part of which is shown logically in FIG. 11B as architecture 1305. The HVA client 1308 may make many requests to HVA server 1302. One advantage of the stateless transfer architecture 1305 is that requests, such as request 1307, from the HVA client 1308 to the HVA server 1302 include (i.e., within the request itself) the necessary state information to allow the HVA server 1302 to respond properly to the requests. After the HVA server 1302 has completed its processing, the appropriate state is communicated back to the HVA client 1308 in response 1309. In this regard, "state" refers to data required to fulfil or respond to, the request 1307. "State" is data that varies by patient, physician, and other entities, and by diagnosis and other factors and considerations. Thus, "state" refers to data in, for example, EMR system 1304, or data resident on the HVA server 1302. As a further example, "state" may refer to authentication information passed from the HVA client 1308 to the HVA server 1302. The request 1307 is seen to include a URI 1307A as well as a body 1307B. The necessary state information may be contained within the URI 1307A. The URI 1307A uniquely identifies the source (HVA client application 1308) and the state, or state change, of the HVA client 1308. The state information also may be included in a header or in the body 1307B. The architecture 1305, therefore, eliminates the concept of a "session," where the HVA server 1302 would be required to maintain, update, and communicate session state. Thus, the HVA server 1302 operates more efficiently, and load balancing is less of a concern with the "stateless" nature of the architecture 1305. Use of the architecture 1305 also reduces problems with "lost" data and responses when the HVA client 1308 is implemented as a browser plug-in.

Figure 11C:
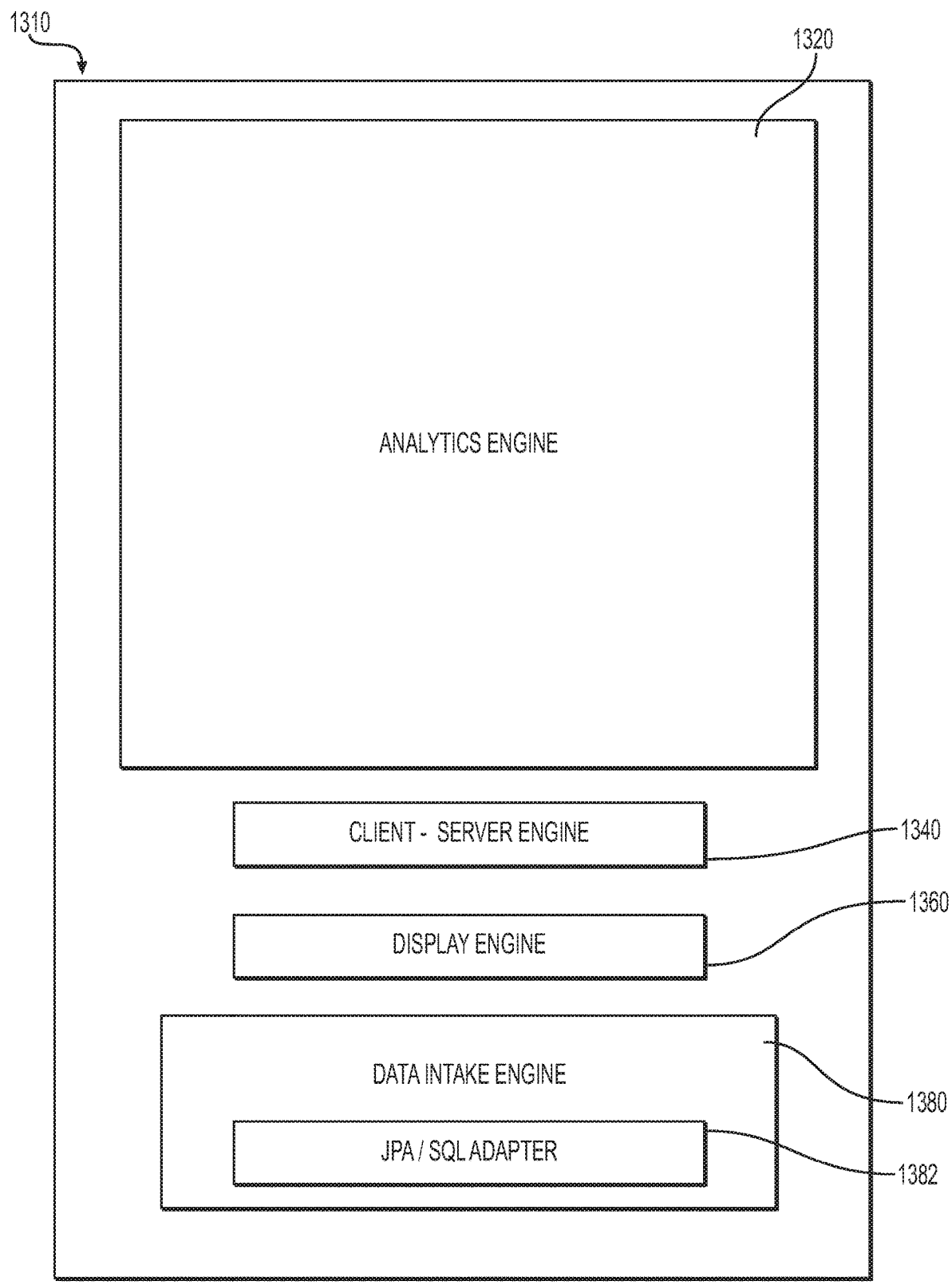

FIG. 11C illustrates an example program of instructions executable by processors accessible by the HVA client 1308 and the HVA server 1302. In FIG. 11C, program 1310 includes components (modules, engines, data) that may be distributed between and among HVA client 1308, the HVA server 1302, and other workstations and processing and data storage devices, including those shown in the example system 1300 of FIG. 11A. Moreover, the example program 1310 shown in FIG. 11C is for illustration purposes, and the various components of the program 1310 may be combined or separated. The program 1310 includes analytics engine 1320, client-server engine 1340, display engine 1360, and data intake engine 1380. The analytics engine 1320 includes analytics module 1322, which includes analytics models, machine learning module 1324, baseline module 1326, cost module 1328, which includes cost models, predictor module 1132, and disambiguation module 1134. The client-server engine 1340, in an embodiment, employs the stateless transfer architecture 1305 of FIG. 11B to allow efficient, accurate communications (requests and responses) between the HVA client 1308 and the HVA server 1302. The client-server engine 1340 is shown in more detail in FIG. 11D. The display engine 1360 includes display drivers to display the progress bar and other data. The data intake engine 1380 includes JPA/SQL adapter module 1382 and an HVAAnalytics.jar executable to allow communications and data transfer between the HVA server 1302 and the EMR system 1304.

The HVA server 1302, in cooperation with the HVA client 1308, and other components of the system 1300 of FIG. 11A, executes components of the program 1310 to display interfaces such as the displays of FIGS. 3, 4A, 4B, and 8A-8C.

The HVA Server 1302 also executes the program 1310 to develop or use specific models, to populate specific data stores, to analyze data using the models, and to interact with the HVA client 1308 and the EMR system 1304 using procedures similar to those disclosed with respect to the program 510 of FIG. 5C.

In an embodiment, the HVA client application 1308 enables a display that is the same as or similar to the display 300 of FIG. 3, the display 400 of FIG. 4A, the display 424 of FIG. 4B, or the displays of FIGS. 8A-8C.

The system 1300 operates in real-time or nearly real-time, such that changes to data in various components of the system 1300 may be reflected in other components concurrently or within a short period after the change. For example, whenever data from the EMR system 1304 for a patient record that is currently on display at the HVA client 1308 is updated with new information relating to either the DRG or the orders/costs associated with the patient, the system 1300 becomes aware of the data changes within a short period (e.g., 15 seconds) of the change and presents updated HVA value content on the display of the HVA client application 1308. Example mechanisms to "make the system 1300 aware" are disclosed herein, including with respect to the description of FIG. 11D.

Components of the system 1300 may monitor changes in the treatment plans by periodically comparing the latest measured values against the baselines. The components may use configurable threshold ranges to define notification events that may be sent to a subscribing endpoint (by, for example email, message queues, http, etc.). Example endpoints displayed through the system 1300 of FIG. 11A include an account of physician provider (who may access the account using the EMR user interface client 1303).

To provide an alerting function (such as display 830 of FIG. 8C), update the value continuum in real time, and reduce bandwidth demand on the network of FIG. 11A (the network being the connections between and among the components of system 1300, and in particular, the connections between and among the EMR user interface client 1303, HVA client 1108, HVA server 1302, and EMR system 1304), queries, requests, and demands on the EMR system 1304 database, and general computational load on the EMR system 1304, may be handled in such a way that some activity by a physician/healthcare professional (the physician provider) may be handled before the HVA client 1308 is able to request an update to the value bar. In an aspect, the required "activity" may be a browser event, such as clicking on the value bar, for example. Such browser activity may be detected by an event listener and the resulting action may be invoked through operation of an event handler. Such event listener and event handler are disclosed here, for example, with respect to FIG. 11D.

Figure 11D:
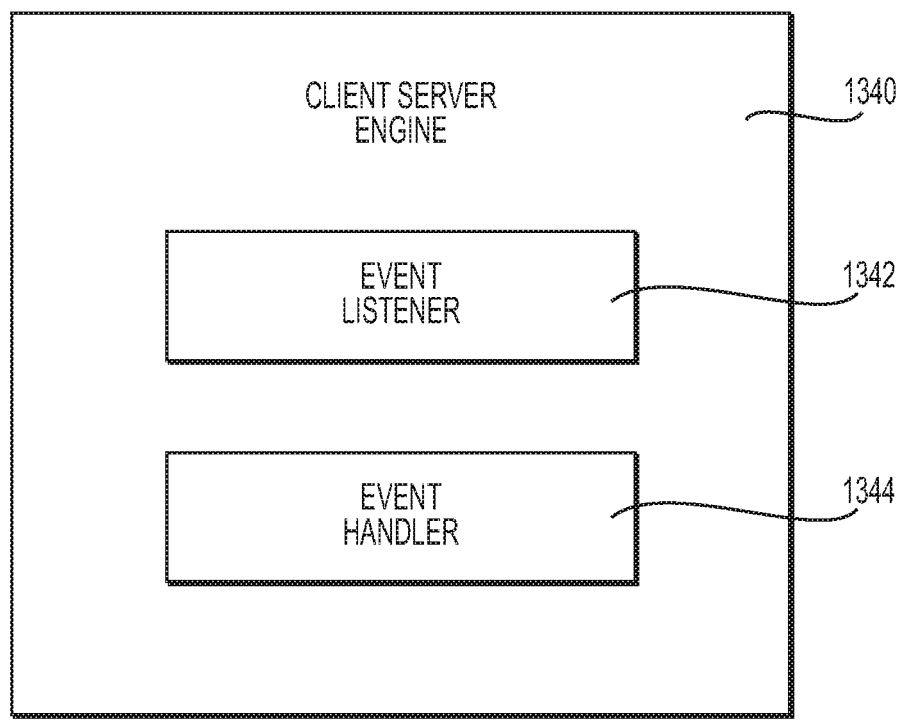

FIG. 11D illustrates an example client server engine 1340. The client server engine 1340 includes event listener 1342 and event handler 1344. To improve network traffic efficiency, the EMR user interface client 1303 uses the event listener 1342 to detect an activity indicative of an appropriate browser event, such as navigate, refresh, etc. In one example, the physician provider using the device 1301A may log in to the system 1300 (i.e., may operate the EMR user interface client 1303, access the CPOE module 1304A, and enter an order for a newly-admitted patient). The HVA client 1308, invoking event listener 1342, identifies the log-in and order entry as activity that calls for creation of a value continuum and corresponding progress bar, and sends a request 1307 to the HVA server 1302, which in turn executes instructions to create and display the value continuum and the corresponding progress bar. In a second example, when a link is clicked-on or the browser is refreshed, the client 1303 validates that the URL is the correct address of the EMR system 1304. Aspects of this second example include the event listener 1342 detecting the click on, or navigate, to another page or to another URL as an activity or event that may require recomputation of the cost to treat that is reflected in the value continuum and expressed by the progress bar. However, not all click-on detections result in a need to recompute the cost to treat. The event handler 1344 may account for such events by invoking a "minimal request" process. For example, as the client 1303 is navigated through the EMR system 1304, with the same patient selected, on each event the client 1303 may use a minimal request to the HVA server 1302 asking for an update to the cost value. If the value returned is the same as the current value, no further network transmissions are performed until another browser event is detected. If the cost values differ, then the client 1303 may request an update for the rest of the patient information such as DRG, DRG description, detailed cost breakdown, etc. However, the request is only for data that has changed. In this method, the network utilization of the client device is tied to comparing the currently stored cost on the client side with an updated cost on the server side. Furthermore, in a scenario where the client side EMR is using a web browser and hosts the EMR system 1304 at a specific URL, the HVA client application 1308 may compare the current URL being viewed by the user to the EMR system 1304 host URL to determine if it is appropriate to both display and populate (request patient information from the HVA server 1302) the value continuum and progress bar. For example; while a user is viewing a patient, in the EMR system 1304 via a web browser, who has a valid working DRG, the user will see a populated value continuum. But if that user navigates to www.xxxxx.com, the HVA client 1308 may recognize the new URL as an invalid URL; i.e., not a URL that is used to host the browser based EMR system 1304. Therefore, the HVA client 1308 will no longer display the value continuum and progress bar, nor will the HVA client 1308 make any further requests to the HVA server 1302 nor create any more network traffic. In a browser-based EMR system, the URL that hosts the EMR system may be hard coded in the HVA client 1308. While accessing the EMR system 1304, a user may navigate through many links to get different information e.g., create a new order for a patient, see the fulfillment of standing orders, see documentation of a patient, see allergy information of a patient, etc. Clicking in any of these links would initiate a navigation event. Either the user (through a user device, for example) or the EMR system 1304 itself may initiate a navigation or refresh event. In an example instantiation of the EMR system 1304, the EMR client application 1308 may use iframes, and the HAV client 1108 may detect a navigation event, whether the user navigates to a completely new URL, or the user navigates to a new frame that is within the EMR system 1304 URL. A minimal request may be a GET request sent to the HVA server 1302 to retrieve current cost value for a patient using only the necessary information to be sent to the HVA server 1302 to fulfill the request to get the current running cost of the patient. In an aspect, HVA client 1308 analyzes events that are detectable on the client side without utilizing any network resources. To perform a similar analysis on the server side, the HVA server 1302 would have to constantly poll the client side for new event information, which would use more network bandwidth. As noted herein, network utilization is at a premium in a hospital's network. Therefore, in the system 1300, the HVA server 1302 acts as a slave to requests from the HVA client 1308, and the HVA server 1302 is able to efficiently deliver value and cost details at the request of the HVA client 1308. The notion of using event listeners/handlers in the HVA client 1308 is useful in systems that use a browser-based EMR interface. In other scenarios, the HVA client 1308 may use screen captures and analyze text to validate and distinguish update events of standalone EMR software.

The disclosed embodiments are also particularly useful for prepaid or bundled medical services, including, but not limited to, health maintenance organizations (HMOs) and clinically integrated networks (CINs). In these environments, the disclosed progress bar may track costs for a defined period against a contracted prepaid or bundled amount. As services are deployed and resources are consumed, a health care provider may quickly see exactly how the provider is performing in the value of care continuum for each patient with prepaid or bundled medical services.

As described above, embodiments of this disclosure provide the ability to link the cost side of patient care at the point of the provider with the reimbursement side of the patient care from the third party payer. Once the expected reimbursement is determined, that information will be entered into the system. The disclosed embodiments also provide the ability to link actual costs with estimated costs to treat. As the primary driver of cost, the physician or other health care provider is able to monitor in relative terms or in precise terms the cost of his care during each phase of the care continuum. By linking the physician with these financial components, improved awareness and greater value for care provided will result in finally bending the cost of the health care curve downward.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data may be permanently stored and media where data may be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit" and "receive," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

We claim:

1. A method, implemented on a client-server architecture comprising a plurality of physician computing devices and one or more central servers, each server comprising a processor, for improving a physician's workflow including by determining and indicating values of medical treatment plans, comprising:

a health value analytics (HVA) system comprising an HVA server and a plurality of HVA client applications, the HVA server comprising a processor, the HVA server creating value baselines comprising health metric values for approved plans of care;

the HVA system detecting a first activity occurring at an electronic medical record (EMR) server, the EMR server separate and distinct from the HVA system, the HVA system and the EMR server connected through a local private network, the first activity indicating a patient-related event occurring during a visit associated with a patient, comprising:

an HVA client application, provided by the HVA server and instantiated as a thin-client on a physician's computing device, detecting, at the physician's computing device, a communication from the physician's computing device to the EMR server, the communication comprising the first activity, the HVA client application detecting a physical location of a display of an electronic medical record for the patient in an EMR page on a display screen of the physician's computing device, and the HVA client application providing the communication and the physical location to the HVA server;

in response to the detected first activity, the HVA server generating a health value continuum for the patient and generating a comparison of the health value continuum to a value baseline; and in response to the electronic medical record physical location, the HVA server providing data and instructions to display and maintain displayed at the physician's computing device on an HVA display page, a representation of the health value continuum to value baseline comparison at a location adjacent to the EMR page, comprising:

placing the representation of the health value continuum to the value baseline adjacent to the EMR page for the patient, monitoring activity on the physician's computing device related to the electronic medical record of the patient, and terminating the display of the health value continuum to the value baseline upon the HVA client application detecting a second activity comprising termination of the display of the electronic medical record of the patient and display of a second electronic medical record for a second patient.

2. The method of claim 1, wherein the patient-related event comprises a patient visit that has an associated diagnosis.

3. The method of claim 1, comprising:
detecting re-display of the electronic medical record for the patient on the EMR page of the physician's computing device;
maintaining terminated, the display of the health value continuum to the value baseline comparison;
detecting a third activity comprising a medical treatment order for the patient; and
providing updated data and instructions to display an update of the representation of the health value continuum to value baseline comparison for display adjacent to the EMR page for the patient.

4. The method of claim 3, wherein the second activity comprises a change to a cost basis of the health value continuum.

5. The method of claim 1, wherein the second activity comprises navigation away from the EMR page for the patient and to a second EMR page for the second patient.

6. The method of claim 3, wherein the physician's computing device and the processors are connected through a client-server system, and wherein the update comprises minimal changes to the representation of the health value continuum to value baseline comparison.

7. A method executed over a client-server architecture in a local private network, the local private network connecting an electronic medical record (EMR) system and a health value analytics (HVA) system, the EMR system comprising an EMR server and EMR client devices, the HVA system, separate from the EMR system and comprising an HVA server and thin-client HVA applications, the method, comprising:

creating by the HVA server, value baselines comprising health metric values for approved plans of care;
receiving by the HVA server, detected and provided by execution of a thin-client HVA application instantiated on an EMR client device, a detected first activity related to medical care for a patient having an associated diagnosis during a visit of the patient; and
the HVA server:
generating a health value continuum corresponding to the diagnosis,
generating a comparison of the health value continuum to the value baseline, and
providing data and instructions to display and maintain displayed a representation of the health value continuum to value baseline comparison on an HVA display page in a position adjacent to an EMR display page displayed on the EMR client device, the EMR display page including an EMR display for the patient, comprising:
receiving a physical location of the EMR display page determined by execution of the thin-client HVA application,
placing the representation of the health value continuum to the value baseline adjacent to the EMR display for the patient, and
terminating the display of the health value continuum to the value baseline upon the thin-client HVA client application detecting a second activity comprising termination of the display of the electronic medical record of the patient and display of a second electronic medical record for a second patient.

8. The method of claim 7, wherein the EMR client and the EMR server are invoked on a single hardware platform.

9. The method of claim 7, wherein the HVA server provides data and instructions to invoke updates to the representation of the health value continuum to value baseline comparison.

10. The method of claim 9, wherein the EMR client and HVA server execute a quality of service protocol in which updates are placed in queue first in order of priority and second in order of generation.

11. A method executed by a processor of a health value analytics (HVA) system in communication an electronic medical record (EMR) device external to the HVA system for improving physicians' workflows, the method, comprising:

an HVA server receiving, by execution of a thin-client HVA application instantiated on the EMR device, an indication of a patient-related event, the patient-related event referencing a visit of a patient; and
based on a visit reference, the processor:
generating of a comparison of the health value continuum to a value baseline for an approved plan of care for the patient, and providing the comparison and instructions to display on a display of the EMR device, the display including an EMR for the patient, a representation of the health value continuum to value baseline comparison, comprising:
  receiving a detection, sent by the thin-client HVA application, a physical location of the EMR for the patient on the EMR display,
    providing instructions to place the representation of the health value continuum to the value baseline adjacent to the EMR for the patient, and
    terminating the display of the health value continuum to the value baseline upon the thin-client HVA client application detecting a second activity comprising termination of the display of the EMR for the patient and display of a second EMR for a second patient.

12. The method of claim 11, comprising:
  receiving from the EMR device, a second indication of a second patient-related event;
  determining a need to provide an updated continuum update based on the second patient-related event;
  generating an update to the health value continuum and the comparison; and
  providing data and instructions to the EMR device to display on a display page, a representation of the update to the comparison.

13. The method of claim 11, the comparison comprising a progress bar showing a current relation between the value baseline and the value continuum, the progress bar indicating a cost to date to treat the patient.

14. The method of claim 13, wherein the comparison is based on a baseline value of historical patient-related events.

15. The method of claim 14, comprising the HVA server generating the value baseline, wherein the patient-related event comprises one or more of:
  admission of the patient to a hospital;
  a diagnosis of a medical condition of the patient; and
  one or more orders to treat the medical condition, the one or more orders comprising a medical treatment plan for the patient, and wherein the value continuum comprises a cost for each of the one or more orders.

16. The method of claim 15, wherein the HVA server generating a value continuum comprises the HVA server determining the patient-related event comprises one of creating a cost to treat the patient, and changing a cost to treat the patient.

17. An improved physician's workflow method implemented on a client-server architecture comprising client devices and central servers in a local private network, the method, comprising:
  receiving, in an electronic medical record (EMR) system comprising an EMR server and associated EMR processor, the EMR system accessible by a physician using a physician's computing device, a log in and an identification of a patient sent from the physician's computing device;
  authenticating the log in;
  providing electronic medical records for the patient for display on an EMR page on the physician's computing device;
  installing, on the physician's computing device, a thin-client Health Value Analytics (HVA) application received from an HVA server of an HVA system, the HVA server coupled to the local private network;
  executing the thin-client HVA application to:
    detect the log in and a receipt of the electronic medical records for display on the physician's computing device,
    determine a location of the displayed electronic medical record on a display screen of the physician's computing device,
    notify the HVA server of the log in, the receipt and the location, and
    the thin-client HVA application further executed to detect and report to the HVA server, a first activity related to a medical condition of the patient;
  receiving at the physician's computing device, from the HVA server in response to the detection of the first activity, a first comparison of a health value continuum and a value baseline based on the medical condition of the patient and instructions to display the first comparison adjacent to the EMR display page;
  displaying and maintaining displayed the first comparison adjacent to the EMR display page until detection, by the thin-client HVA application, of termination of display of the electronic medical record on the patient on the EMR page; and
  terminating the display of the health value continuum to the value baseline upon the thin-client HVA client application detecting a second activity comprising termination of the display of the electronic medical record of the patient and display of a second electronic medical record for a second patient.

18. The method of claim 17, wherein the first activity comprises a patient visit that has an associated diagnosis.

19. The method of claim 18, comprising:
  detecting by the thin-client HVA application a second activity related to the medical condition of the patient; and
  the thin-client application executing to request from the HVA server, data and instructions to provide an update of a representation of the health value continuum to value baseline comparison.

20. The method of claim 19, wherein the second activity comprises a change to a cost basis of the health value continuum.

21. The method of claim 19, wherein the termination comprises navigation by the physician's computing device to a second electronic medical record for a second patient, and wherein the physician's computing device displays on the EMR page, the second medical record and no display of the health value continuum to value baseline comparison.

22. The method of claim 17, further comprising the thin-client HVA application executing to:
  detect a visit identification (ID) associated with a patient visit;
  convert the visit ID to a digital ID; and
  provided the digital ID with the activity detected notices.

23. The method of claim 17, further comprising the thin-client HVA application executing to:
  wait for a response to an activity detected notice for a set time;
  resend the activity detected notice after the set time when the response is not received; and
  repeat the waiting and resending for a predetermined number of cycles.

* * * * *